United States Patent [19]
Shankar

[11] Patent Number: 5,688,960
[45] Date of Patent: Nov. 18, 1997

[54] SUBSTITUTED OXIMES, HYDRAZONES AND OLEFINS USEFUL AS NEUROKININ ANTAGONISTS

[75] Inventor: Bandarpalle B. Shankar, Branchburg, N.J.

[73] Assignee: Schering Corporation, Kenilworth, N.J.

[21] Appl. No.: 742,013

[22] Filed: Oct. 31, 1996

Related U.S. Application Data

[63] Continuation-in-part of Ser. No. 641,384, Apr. 30, 1996, which is a continuation-in-part of Ser. No. 460,819, Jun. 1, 1995, abandoned, which is a continuation-in-part of Ser. No. 432,740, May 2, 1995, abandoned.

[51] Int. Cl.$^6$ .................... C07D 409/06; A61K 31/445
[52] U.S. Cl. ............................ 546/202; 514/324
[58] Field of Search .................. 546/202; 514/324

[56] References Cited

U.S. PATENT DOCUMENTS 5,350,852  9/1994  Emonds-Alt et al. .................. 544/336

FOREIGN PATENT DOCUMENTS

| | | |
|---|---|---|
| 630887 | 12/1994 | European Pat. Off. . |
| 0 680 962 | 11/1995 | European Pat. Off. . |
| 0 699 674 | 3/1996 | European Pat. Off. . |
| 2717802 | 9/1995 | France . |
| 2274777 | 8/1994 | United Kingdom . |
| WO93/01160 | 1/1993 | WIPO . |
| WO93/01169 | 1/1993 | WIPO . |
| WO93/23380 | 11/1993 | WIPO . |
| WO94/10146 | 5/1994 | WIPO . |
| WO94/20500 | 9/1994 | WIPO . |
| WO95/05377 | 2/1995 | WIPO . |
| WO95/12577 | 5/1995 | WIPO . |

OTHER PUBLICATIONS

Chung et al, *Molecular Pharmacol.*, 48 (1995), pp. 711–716.

Primary Examiner—C. Warren Ivy
Assistant Examiner—Charanjit S. Aulakh
Attorney, Agent, or Firm—Anita W. Magatti

[57] ABSTRACT

Compound represented by the structural formula or a pharmaceutically acceptable salt thereof, wherein:

a is 0, 1, 2 or 3;

b, d and e are independently 0, 1 or 2;

R is H, $C_{1-6}$ alkyl, —OH or $C_2$–$C_6$ hydroxyalkyl;

A is an optionally substituted oxime, hydrazone or olefin;

X is a bond, —C(O)—, —O—, —NR$^6$—, —S(O)$_e$—, —N(R$^6$)C(O)—, —C(O)N(R$^6$)— —OC(O)NR$^6$—, —OC(=S)NR$^6$—, —N(R$^6$)C(=S)O—, —C(=NOR$^1$)—, —S(O)$_2$N(R$^6$)—, —N(R$^6$)S(O)$_2$—, —N(R$^6$)C(O)O— or —OC(O)—;

T is H, phthalimidyl, aryl, heterocycloalkyl, heteroaryl, cycloalkyl or bridged cycloalkyl;

Q is heteroaryl;

$R^{6a}$, $R^{7a}$, $R^{8a}$, $R^{9a}$, $R^6$ and $R^7$ are H, $C_{1-6}$ alkyl, $C_2$–$C_6$ hydroxyalkyl, $C_1$–$C_6$ alkoxy-$C_1$–$C_6$ alkyl, phenyl or benzyl; or $R^6$ and $R^7$, together with the nitrogen to which they are attached, form a ring;

$R^{9a}$ is $R^6$ or —OR$^6$;

Z is morpholinyl, optionally N-substituted piperazinyl, optionally substituted or substituted g is 0–3 and h is 1–4, provided the sum of h and g is 1–7; wherein aryl, heterocycloalkyl, heteroaryl, cycloalkyl and bridged cycloalkyl groups are optionally substituted; methods of treating asthma, cough, bronchospasm, inflammatory diseases, and gastrointestinal disorders with said compounds, and pharmaceutical compositions comprising said compounds are disclosed.

23 Claims, No Drawings

5,688,960

SUBSTITUTED OXIMES, HYDRAZONES AND OLEFINS USEFUL AS NEUROKININ ANTAGONISTS

CROSS REFERENCE TO RELATED APPLICATION

This is a continuation-in-part of U.S. Ser. No. 08/641,384, filed Apr. 30, 1996, which is a continuation in part of U.S. Ser. No. 08/460,819, filed Jun. 1, 1995 now abandoned, which is a continuation-in-part of U.S. Ser. No. 08/432,740, filed May 2, 1995, abandoned.

BACKGROUND OF THE INVENTION

The present invention relates to a genus of substituted oximes, hydrazones and olefins useful as antagonists of tachykinin receptors, in particular as antagonists of the neuropeptides neurokinin-1 receptor ($NK_1$) and/or neurokinin-2 receptor ($NK_2$) and/or neurokinin-3 receptor ($NK_3$).

Neurokinin receptors are found in the nervous system and the circulatory system and peripheral tissues of mammals, and therefore are involved in a variety of biological processes. Neurokinin receptor antagonists are consequently expected to be useful in the treatment or prevention of various mammalian disease states, for example asthma, cough, bronchospasm, inflammatory diseases such as arthritis, central nervous system conditions such as migraine and epilepsy, nociception, and various gastrointestinal disorders such as Crohn's disease.

In particular, $NK_1$ receptors have been reported to be involved in microvascular leakage and mucus secretion, and $NK_2$ receptors have been associated with smooth muscle contraction, making $NK_1$ and $NK_2$ receptor antagonists especially useful in the treatment and prevention of asthma.

Some $NK_1$ and $NK_2$ receptor antagonists have previously been disclosed: arylalkylamines were disclosed in U.S. Pat. No. 5,350,852, issued Sep. 27, 1994, and spiro-substituted azacycles were disclosed in WO 94/29309, published Dec. 22, 1994.

SUMMARY OF THE INVENTION

Compounds of the present invention are represented by the formula I

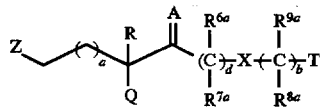

or a pharmaceutically acceptable salt thereof, wherein:

a is 0, 1, 2 or 3;

b and d are independently 0, 1 or 2;

R is H, $C_{1-6}$ alkyl, —$OR^6$ or $C_2$–$C_6$ hydroxyalkyl;

A is =N—$OR^1$, =N—$N(R^2)(R^3)$, =$C(R^{11})(R^{12})$ or =$NR^{25}$;

X is a bond, —C(O)—, —O—, —$NR^6$—, —$S(O)_e$—, —$N(R^6)C(O)$—, —$C(O)N(R^6)$——$OC(O)NR^6$—, —OC(=S)$NR^6$—, —$N(R^6)C(=S)O$—, —C(=$NOR^1$)—, —$S(O)_2N(R^6)$—, —$N(R^6)S(O)_2$—, —$N(R^6)C(O)O$— or —OC(O)—, provided that when d is 0, X is a bond, —C(O)—, —$NR^6$—, —$C(O)N(R^6)$—, —$N(R^6)C(O)$—, —OC(O)$NR^6$—, —C(=$NOR^1$)—, —$N(R^6)C(=S)O$—, —OC(=S) $NR^6$—, —$N(R^6)S(O)_2$— or —$N(R^6)C(O)O$—; provided that when A is =$C(R^{11})(R^{12})$ and d is 0, X is not —$NR^6$— or —$N(R^6)C(O)$—; and provided that when A is =$NR^{25}$, d is 0 and X is —$NR^6$— or —$N(R^6)C$ (O)—;

T is H, $R^4$-aryl, $R^4$-heterocycloalkyl, $R^4$-heteroaryl, phthalimidyl, $R^4$-cycloalkyl or $R^{10}$-bridged cycloalkyl;

Q is $R^5$-heteroaryl;

$R^1$ is H, $C_{1-6}$ alkyl, —$(C(R^6)(R^7))_n$—G, —$G^2$, —$(C(R^6)(R^7))_p$—M— $(C(R^{13})(R^{14}))_n$—$(C(R^8)(R^9))_u$—G, —C(O)N($R_6$)—$(C(R^{13})(R^{14}))_n$—$(C(R^8)(R^9))_u$—G or —$(C(R^6)(R^7))_p$—M—($R^4$-heteroaryl);

$R^2$ and $R^3$ are independently selected from the group consisting of H, $C_{1-6}$ alkyl, —CN, —$(C(R^6)(R^7))_n$—G, —$G^2$, —C(O)—$(C(R^8)(R^9))_n$—G and —$S(O)_e R^{13}$; or $R^2$ and $R^3$, together with the nitrogen to which they are attached, form a ring of 5 to 6 members, wherein 0, 1 or 2 ring members are selected from the group consisting of —O—, —S— and —$N(R^{19})$—;

$R^4$ and $R^5$ are independently 1–3 substituents independently selected from the group consisting of H, halogeno, —$OR^6$, —$OC(O)R^6$, —$OC(O)N(R^6)(R^7)$, —$N(R^6)(R^7)$, $C_{1-6}$ alkyl, —$CF_3$, —$C_2F_5$, —$COR^6$, —$CO_2R^6$, —$CON(R^6)(R^7)$, —$S(O)_e R^{13}$, —CN, —$OCF_3$, —$NR^6CO_2R^{16}$, —$NR^6COR^7$, —$NR^8CON$ $(R^6)(R^7)$, $R^{15}$-phenyl, $R^{15}$-benzyl, $NO_2$, —$N(R^6)S(O)_2$ $R^{13}$ or —$S(O)_2N(R^6)(R^7)$; or adjacent $R^4$ substituents or adjacent $R^5$ substituents can form a —O—$CH_2$—O— group; and $R^4$ can also be $R^{15}$-heteroaryl;

$R^6$, $R^7$, $R^8$, $R^{6a}$, $R^{7a}$, $R^{8a}$, $R^{13}$ and $R^{14}$ are independently selected from the group consisting of H, $C_{1-6}$ alkyl, $C_2$–$C_6$ hydroxyalkyl, $C_1$–$C_6$ alkoxy-$C_1$–$C_6$ alkyl, $R^{15}$-phenyl, and $R^{15}$-benzyl; or $R^6$ and $R^7$, together with the nitrogen to which they are attached, form a ring of 5 to 6 members, wherein 0, 1 or 2 ring members are selected from the group consisting of —O—, —S— and —$N(R^{19})$—;

$R^9$ and $R^{9a}$ are independently selected from the group consisting of $R^6$ and —$OR^6$ $R^{10}$ and $R^{10a}$ are independently selected from the group consisting of H and $C_{1-6}$ alkyl;

$R^{11}$ and $R^{12}$ are independently selected from the group consisting of H, $C_1$–$C_6$ alkyl, —$CO_2R^6$, —$OR^6$, —$C(O)N(R^6)(R^7)$, $C_1$–$C_6$ hydroxyalkyl, —$(CH_2)_r$—$OC(O)R^6$, —$(CH_2)_r$—$OC(O)CH=CH_2$, —$(CH_2)_r$—O $(CH_2)_s$—$CO_2R^6$, —$(CH_2)_r$—O—$(CH_2)_s$—$C(O)N(R^6)$ $(R^7)$ and —$(CH_2)_r$—$N(R^6)(R^7)$;

$R^{15}$ is 1 to 3 substituents independently selected from the group consisting of H, $C_1$–$C_6$ alkyl, $C_1$–$C_6$ alkoxy, $C_1$–$C_6$ alkylthio, halogeno, —$CF_3$, —$C_2F_5$, —$COR^{10}$, —$CO_2R^{10}$, —$C(O)N(R^{10})_2$, —$S(O)_e R^{10a}$, —CN, —$N(R^{10})COR^{10}$, —$N(R^{10})CON(R^{10})_2$ and —$NO_2$;

$R^{16}$ is $C_{1-6}$ alkyl, $R^{15}$-phenyl or $R^{15}$-benzyl;

$R^{19}$ is H, $C_1$–$C_6$ alkyl, —$C(O)N(R^{10})_2$, —$CO_2R^{10}$, —(C $(R^8)(R^9))_f$—$CO_2R^{10}$ or —$(C(R^8)(R^9))_u$—$C(O)N$ $(R^{10})_2$;

f, n, p, r and s are independently 1–6;

u is 0–6;

G is selected from the group consisting of H, $R^4$-aryl, $R^4$-heterocycloalkyl, $R^4$-heteroaryl, $R^4$-cycloalkyl, —$OR^6$, —$N(R^6)(R^7)$, —$COR^6$, —$CO_2R^6$, —$CON(R^7)$ $(R^9)$, —$S(O)_e R^{13}$, —$NR^6CO_2R^{16}$, —$NR^6COR^7$, —$NR^8CON(R^6)(R^7)$, —$N(R^6)S(O)_2R^{13}$, —$S(O)_2N$ $(R^6)(R^7)$, —$OC(O)R^6$, —$OC(O)N(R^6)(R^7)$, —C(=$NOR^8$)$N(R^6)(R^7)$, —C(=$NR^{25}$)$N(R^6)(R^7)$, —$N(R^8)C(=NR^{25})N(R^6)(R^7)$, —CN, —$C(O)N(R^6)$ $OR^7$, and —$C(O)N(R^9)$—($R^4$-heteroaryl), provided that when n is 1 and u is 0, or when $R^9$ is —$OR^6$, G is not —OH or —$N(R^6)(R^7)$;

M is selected from the group consisting of a double bond, —O—, —$N(R^6)$—, —C(O)—, —$C(R^6)(OR^7)$—, —$C(R^8)(N(R^6)(R^7))$—, —$C(=NOR^6)N(R^7)$—, —$C(N(R^6)(R^7))=NO$—, —$C(=NR^{25})N(R^6)$—, —$C(O)N(R^9)$—, —$N(R^9)C(O)$—, —$C(=S)N(R^9)$—, —$N(R^9)C(=S)$— and —$N(R^6)C(O)N(R^7)$—, provided that when n is 1, G is not OH or —$NH(R^6)$; and when p is 2–6, M can also be —$N(R^6)C(=NR^{25})N(R^7)$— or —$OC(O)N(R^6)$—;

$G^2$ is $R^4$-aryl, $R^4$-heterocycloalkyl, $R^4$-heteroaryl, $R^4$-cycloalkyl, —$COR^6$, —$CO_2R^{16}$, —$S(O)_2N(R^6)(R^7)$ or —$CON(R^6)(R^7)$;

e is 0–2, provided that when e is 1 or 2, $R^{13}$ and $R^{10a}$ are not H;

$R^{25}$ is H, $C_1$–$C_6$ alkyl, —CN, $R^{15}$-phenyl or $R^{15}$-benzyl;

Z is

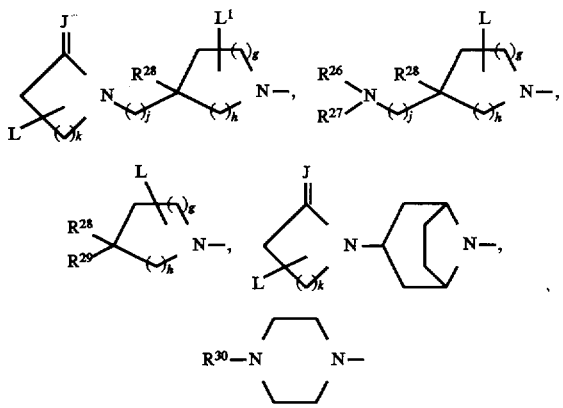

or morpholinyl;

g and j are independently 0–3;

h and k are independently 1–4, provided the sum of h and g is 1–7;

J is two hydrogen atoms, =O, =S, =$NR^9$ or =$NOR^1$;

L and $L^1$ are independently selected from the group consisting of H, $C_1$–$C_6$ alkyl, $C_1$–$C_6$ alkenyl, —$CH_2$-cycloalkyl, $R^{15}$-benzyl, $R^{15}$-heteroaryl, —$C(O)R^6$, —$(CH_2)_m$—$OR^6$, —$(CH_2)_m$—$N(R^6)(R^7)$, —$(CH_2)_m$—$C(O)$—$OR^6$ and —$(CH_2)_m$—$C(O)N(R^6)(R^7)$;

m is 0 to 4, provided that when j is 0, m is 1–4;

$R^{26}$ and $R^{27}$ are independently selected from the group consisting of H, $C_1$–$C_6$ alkyl, $R^4$-aryl and $R^4$-heteroaryl; or $R^{26}$ is H, $C_1$–$C_6$ alkyl, $R^4$-aryl or $R^4$-heteroaryl, and $R^{27}$ is —$C(O)R^6$, —$C(O)$—$N(R^6)(R^7)$, —$C(O)(R^4$-aryl), —$C(O)(R^4$-heteroaryl), —$SO_2R^{13}$ or —$SO_2$—$(R^4$-aryl);

$R^{28}$ is H, —$(C(R^6)(R^{19}))_t$—G, —$(C(R^6)(R^7))_v$—$G^2$ or —$NO_2$;

t and v are 0, 1, 2 or 3, provided that when j is 0, t is 1, 2 or 3;

$R^{29}$ is H, $C_1$–$C_6$ alkyl, —$C(R^{10})_2S(O)_eR^6$, $R^4$-phenyl or $R^4$-heteroaryl;

$R^{30}$ is H, $C_1$–$C_6$ alkyl, $R^4$-cycloalkyl, —$(C(R^{10})_2)_w$—$(R^4$-phenyl), —$(C(R^{10})_2)_w$—$(R^4$-heteroaryl), —$C(O)R^6$, —$C(O)OR^6$, —$C(O)N(R^6)(R^7)$,

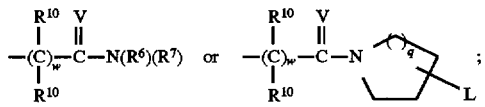

w is 0, 1, 2, or 3;

V is =O, =S or =$NR^6$; and q is 0–4.

Preferred are compounds of formula I wherein X is —O—, —C(O)—, a bond, —$NR^6$—, —$S(O)_e$—, —$N(R^6)C(O)$—, —$OC(O)NR^6$ or —$C(=NOR^1)$—. More preferred are compounds of formula I wherein X is —O—, —$NR^6$—, —$N(R^6)C(O)$— or —$OC(O)NR^6$. Additional preferred definitions are: b is 1 or 2 when X is —O— or —$N(R^6)$—; b is 0 when X is —$N(R^6)C(O)$—; and d is 1 or 2. T is preferably $R^4$-aryl, $R^4$-heteroaryl, $R^4$-cycloalkyl or $R^{10}$-bridged cycloalkyl, with $R^4$-aryl, especially $R^4$-phenyl, being more preferred. Also preferred are compounds wherein $R^{6a}$, $R^{7a}$, $R^{8a}$ and $R^{9a}$ are independently hydrogen, hydroxyalkyl or alkoxyalkyl, with hydrogen being more preferred. Especially preferred are compounds wherein $R^{8a}$ and $R^{9a}$ are each hydrogen, d and b are each 1, X is —O—, —$NR^6$—, —$N(R^6)C(O)$— or —$OC(O)NR^6$, T is $R^4$-aryl and $R^4$ is two substituents selected from $C_1$–$C_6$ alkyl, halogeno, —$CF_3$ and $C_1$–$C_6$ alkoxy. Preferred definitions for T being $R^4$-heteroaryl include $R^4$-quinolinyl and oxadiazolyl.

Also preferred are compounds of formula I wherein R is hydrogen. Q is preferably $R^5$-heteroaryl wherein $R^5$ is hydrogen. An especially preferred definition for Q is benzothienyl.

Preferred are compounds of formula I wherein A is =N—$OR^1$ or =N—$N(R^2)(R^3)$. More preferred are compounds wherein A is =N—$OR^1$. $R^1$ is preferably H, alkyl, —$(CH_2)_n$—G, —$(CH_2)_p$—M—$(CH_2)_n$—G or —$C(O)N(R^6)(R^7)$, wherein M is —O— or —$C(O)N(R^9)$— and G is —$CO_2R^6$, —$OR^6$, —$C(O)N(R^6)(R^9)$, —$C(=NOR^8)N(R^6)(R^7)$, —$C(O)N(R^9)(R^4$-heteroaryl) or $R^4$-heteroaryl. $R^2$ and $R^3$ are independently preferably H, $C_1$–$C_6$ alkyl, —$(C(R^6)(R^7))_n$—G or $G^2$.

Preferred definitions of Z are

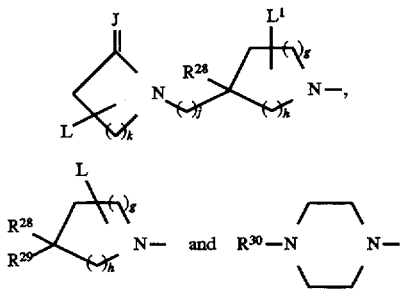

with the following groups being more preferred:

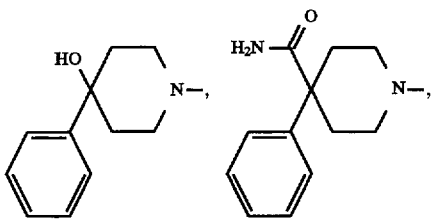

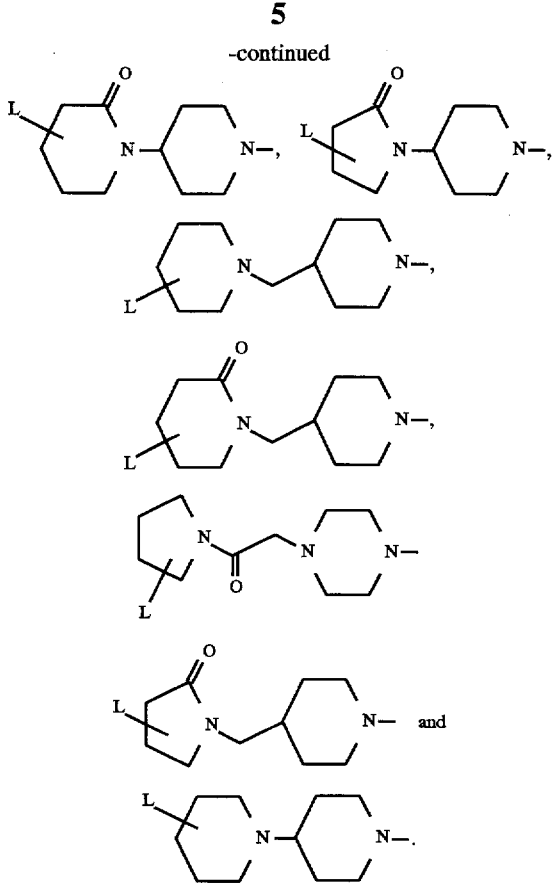

This invention also relates to the use of a compound of formula I in the treatment of asthma, cough, bronchospasm, inflammatory diseases such as arthritis, central nervous system conditions such as migraine and epilepsy, nociception, and various gastrointestinal disorders such as Crohn's disease.

In another aspect, the invention relates to a pharmaceutical composition comprising a compound of formula I in a pharmaceutically acceptable carrier. The invention also relates to the use of said pharmaceutical composition in the treatment of asthma, cough, bronchospasm, inflammatory diseases such as arthritis, migraine, nociception, and various gastrointestinal disorders such as Crohn's disease.

DETAILED DESCRIPTION

As used herein, the term "alkyl" means straight or branched alkyl chains. "Lower alkyl" refers to alkyl chains of 1–6 carbon atoms and, similarly, lower alkoxy refers to alkoxy chains of 1–6 carbon atoms.

"Cycloalkyl" means cyclic alkyl groups having 3 to 6 carbon atoms. "Bridged cycloalkyl" refers to $C_7$–$C_{10}$ saturated rings comprised of a cycloalkyl ring or a fused bicycloalkyl ring and an alkylene chain joined at each end to non-adjacent carbon atoms of the ring or rings. Examples of such bridged bicycloalkyl rings are adamantyl, myrtanyl, noradamantyl, norbornyl, bicyclo[2.2.1]heptyl, 6,6-dimethylbicyclo[3.1.1]heptyl, bicyclo[3.2.1]octyl, and bicyclo[2.2.2]octyl.

"Aryl" means phenyl, naphthyl, indenyl, tetrahydronaphthyl, indanyl, anthracenyl or fluorenyl.

"Halogeno" refers to fluoro, chloro, bromo or iodo atoms.

"Heterocycloalkyl" refers to 4- to 6-membered saturated rings comprising 1 to 3 heteroatoms independently selected from the group consisting of —O—, —S— and —N($R^{19}$)—, with the remaining ring members being carbon. Examples of heterocycloalkyl rings are tetrahydrofuranyl, pyrrolidinyl, piperidinyl, morpholinyl, thiomorpholinyl and piperazinyl. $R^4$-heterocycloalkyl refers to such groups wherein substitutable ring carbon atoms have an $R^4$ substituent.

"Heteroaryl" refers to 5- to 10-membered single or benzofused aromatic rings comprising 1 to 4 heteroatoms independently selected from the group consisting of —O—, —S— and —N=, provided that the rings do not include adjacent oxygen and/or sulfur atoms. Examples of single-ring heteroaryl groups are pyridyl, oxazolyl, isoxazolyl, oxadiazolyl, furanyl, pyrrolyl, thienyl, imidazolyl, pyrazolyl, tetrazolyl, thiazolyl, isothiazolyl, thiadiazolyl, pyrazinyl, pyrimidyl, pyridazinyl and triazolyl. Examples of benzofused heteroaryl groups are indolyl, quinolyl, benzothienyl (i.e., thionaphthenyl), benzimidazolyl, benzofuranyl, benzoxazolyl and benzofurazanyl. N-oxides of nitrogen-containing heteroaryl groups are also included. All positional isomers are contemplated, e.g., 1-pyridyl, 2-pyridyl, 3-pyridyl and 4-pyridyl. $R^4$-heteroaryl refers to such groups wherein substitutable ring carbon atoms have an $R^4$ substituent.

Where $R^2$ and $R^3$ or $R^6$ and $R^7$ substituents on a nitrogen atom form a ring and additional heteroatoms are present, the rings do not include adjacent oxygen and/or sulfur atoms or three adjacent hetero-atoms. Typical rings so formed are morpholinyl, piperazinyl and piperidinyl.

In the structures in the definition of Z, the substituents L and $L^1$ may be present on any substitutable carbon atom, including in the second structure the carbon to which the —N($R^{26}$)($R^{27}$) group is attached.

In the above definitions, wherein variables $R^6$, $R^7$, $R^8$, $R^9$, $R^{10}$, $R^{13}$, $R^{14}$, $R^{15}$ and $R^{30}$, for example, are said to be independently selected from a group of substituents, we mean that $R^6$, $R^7$, $R^8$, $R^9$, $R^{10}$, $R^{13}$, $R^{14}$, $R^{15}$ and $R^{30}$ are independently selected, but also that where an $R^6$, $R^7$, $R^8$, $R^9$, $R^{10}$, $R^{13}$, $R^{14}$, $R^{15}$ or $R^{30}$ variable occurs more than once in a molecule, those occurrences are independently selected (e.g., if R is —$OR^6$— wherein $R^6$ is hydrogen, X can be —N($R^6$)— wherein $R^6$ is ethyl). Similarly, $R^4$ and $R^5$ can be independently selected from a group of substituents, and where more than one $R^4$ and $R^5$ are present, the substitutents are independently selected; those skilled in the art will recognize that the size and nature of the substituent(s) will affect the number of substituents which can be present.

Compounds of formula I can have at least one asymmetrical carbon atom and all isomers, including diastereomers, enantiomers and rotational isomers, as well as E and Z isomers of the oxime, hydrazone and olefin groups, are contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of formula I.

Those skilled in the art will appreciate that for some compounds of formula I, one isomer will show greater pharmacological activity than other isomers.

Compounds of the invention have at least one amino group which can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain compounds of the invention are acidic (e.g., those compounds which possess a carboxyl group). These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

Compounds of formula I can be prepared using methods well known to those skilled in the art. Following are typical procedures for preparing various compounds; the skilled artisan will recognize that other procedures may be applicable, and that the procedures may be suitably modified to prepare other compounds within the scope of formula I.

Procedure A:

Compounds of formula I as defined above can be prepared as shown in the following reaction scheme:

Step 1:

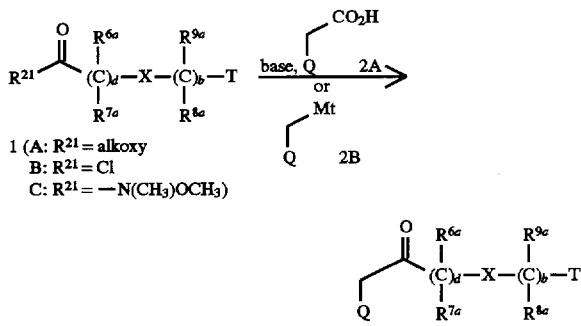

In step 1, a compound of formula 2A, wherein Q is as defined above, is reacted with a base such as lithium diisopropylamide (LDA) or KH in an inert organic solvent such as THF or DME to generate a dianion. An acid chloride, ester or amide of formula 1A, 1B, or 1C is added to give a ketone of formula 3. Preferable reaction temperatures ranges from −78° C. to 30° C.

Alternatively, compounds of formula 3 can be generated by the reaction of a compound of formula 1, preferably 1C, with a metallated species of formula QCH$_2$Mt where Mt is a metal, such as MgHal, wherein "Hal" is halogen, or lithium. The metallated species QCH$_2$Mt can be generated by conventional procedures, such as treatment compounds of formula QCH$_2$Hal with Mg or by treating QCH$_3$ with an organolithium base.

Step 2:

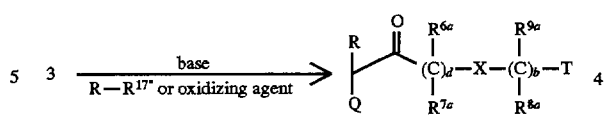

In step 2, for compounds of formula I wherein R is not hydrogen, the ketone 3 is reacted with a suitable base, such as LDA or KH in an inert organic solvent such as THF. For compounds wherein R is alkyl or hydroxyalkyl, a compound R—R$^{17"}$, wherein R$^{17"}$ is leaving group such as Br, I or triflate is added. For compounds wherein R is OH, an appropriate oxidizing agent such as dimethyldioxirane or Davis reagent is added. Preferable reaction temperatures range from −78° to 50° C.

Step 3:

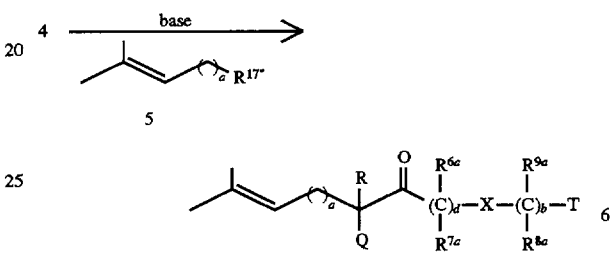

In step 3, ketone 4 is reacted with a base such as LDA in a solvent such as THF, then an olefin of formula 5 is added, wherein R$^{17"}$ is as defined above, to give the adduct 6. Preferable reaction temperatures range from −78° C. to 60° C.

Step 4:

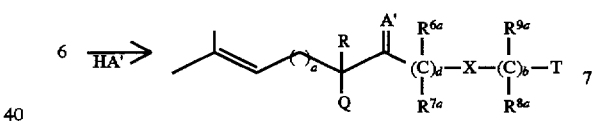

In step 4, ketone 6 is reacted with HA', wherein A' is NH—OR$^1$, NH—N(R$^2$)(R$^3$) or NHR$^{25}$, in an organic solvent such as pyridine at a temperature from 25° C. to 150° C. to give a compound of formula 7.

Step 5:

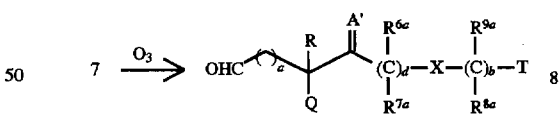

In step 5, a compound of formula 7 is oxidized by ozonolysis to give an aldehyde of formula 8. Suitable organic solvents include EtOAc, ethanol or the like. Preferable reaction temperatures are from −78° to 0° C.

Step 6:

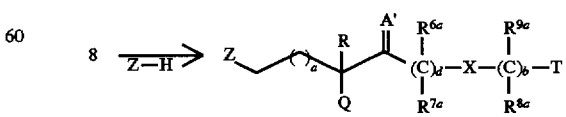

In step 6, an aldehyde of formula 8 is reacted with a compound of formula Z—H, wherein Z is as defined above. Step 6 is preferably carried out with a suitably substituted

9 amine (as its acid salt e.g. HCl or maleate or as its free base) and a hydride source such as NaBH$_3$CN or sodium triacetoxyborohydride in a protic solvent (e.g. CH$_3$OH, CH$_3$CH$_2$OH, or CF$_3$CH$_2$OH) with 3A sieves to obtain the compound of formula I. Any suitable temperature can be used with preferable temperatures between 0° C. and 25° C.

Alternatively, a compound of formula I can be prepared from 6 by the following reaction scheme:

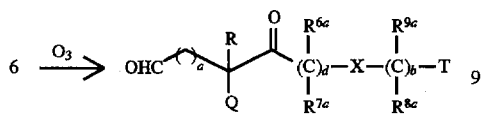

Compound 6 is oxidized to a compound of formula 9 under conditions similar to those described for step 5 above. The aldehyde of formula 9 is reacted with a compound of formula Z—H in a manner similar to that described in Step 6, and the resultant ketone is then reacted with a compound of the formula HA' as described above in Step 4 to obtain the compound of formula I.

Procedure B:

Compounds of formula I wherein X is —O— or a bond and d is 1 or 2 can be prepared by the following reaction scheme, starting with ketone 4 from Procedure A. Alternatively, compounds of formula 4 can be prepared from compounds of formula 1D, wherein X is —O—, $R^{6a}$ and $R^{7a}$ are each H, and d is 1, which, in turn, are prepared according to the either of two following reaction schemes:

Scheme a:

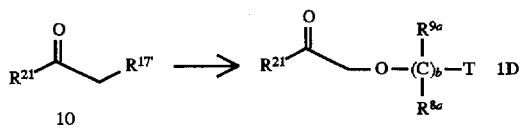

wherein A compound of formula 10, wherein $R^{21}$ is alkoxy or —N(CH$_3$)OCH$_3$ and $R^{17'}$ is as defined above, is reacted with an alcohol of the formula HO—(C($R^{8a}$)($R^{9a}$))$_b$—T in the presence of a suitable base such as Cs$_2$CO$_3$ or KHMDS Scheme b:

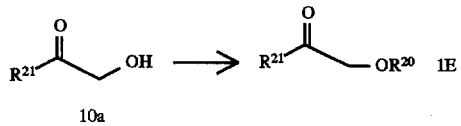

wherein a compound of formula 10a, wherein $R^{21}$ is alkoxy, is reacted with a compound of formula $R^{20}$-$R^{17}$ wherein $R^{17}$ is a leaving group such as Cl or Br and $R^{20}$ is either of the formula

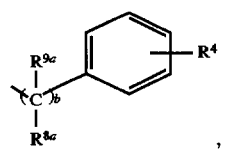

wherein $R^4$, $R^{8a}$, $R^{9a}$ and b are as defined above or $R^{20}$ is trialkyl or diarylalkylsilyl, in the presence of a suitable base such as Cs$_2$CO$_3$, Hunigs's base or KHMDS

10

Step 1:

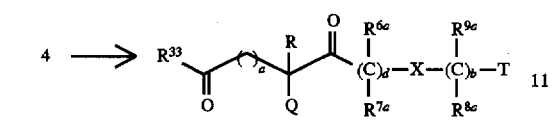

In step 1, compounds of formula 4 treated with an appropriate base, such as NaHDMS, are reacted with alkylating agents of the formula $R^{33}$C(O)CH$_2$$R^{17}$ or $R^{33}$C(O)CH=CH$_2$ wherein $R^{33}$ is alkoxy or —N(CH$_3$)OCH$_3$ and $R^{17}$ is as defined above.

Step 2:

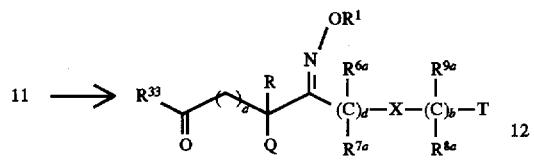

In step 2, compounds of formula 11 can be converted to the corresponding oxime of formula 12 in a manner similar to that described in Procedure A, Step 4.

Step 3:

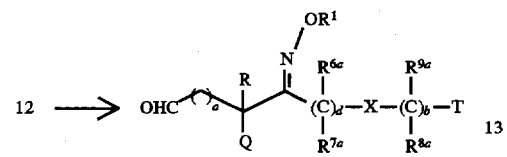

In step 3, a compound of formula 12 (or 11, i.e., wherein A' is O) are convened to the corresponding aldehyde 13 (or lactol from the keto-ester 11) by treatment with a suitable reducing agent such a DIBAL, in an suitable inert organic solvent such as THF, at a temperature from about −100° to −20° C.

Step 4:

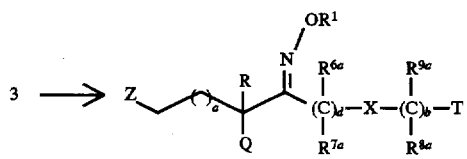

In step 4, compound 13 is reacted with an amine ZH in a manner similar to that described in Procedure A, Step 6, to obtain the compound of formula I.

Alternatively, as shown in the following reaction scheme, compounds of the formula 14, wherein R is H, A' is =O, X is —O— and $R^{33}$ is alkoxy can be convened to the corresponding lactol of formula 15 by treatment with a suitable reducing agent such a DIBAL, in an suitable inert organic solvent such as THF, at a temperature from about −100° to −20° C.:

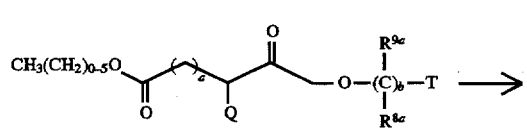

In step 1, oxime alcohol 17 is oxidized with o-iodoxybenzoic acid at room temperature in a solvent such as DMSO or DMF in the presence of an acid such as trifluoroacetic acid.

Step 2:

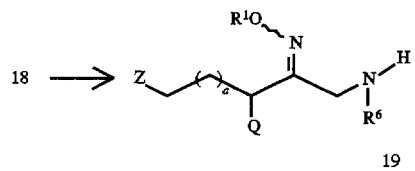

19

In step 2, compound 18 is reacted with an amine $R^6NH$, wherein $R^6$ is as defined above, in an alcohol such as $CH_3OH$, $CH_3CH_2OH$, more preferably $CF_3CH_2OH$, in the presence of a dehydrating agent such as molecular sieves and a reducing agent such as $NaCNBH_3$ to obtain 19.

Step 3:

In step 3, amine 19 can be alkylated, acylated, sulfonylated or reacted with isocyanates to obtain compounds of formula 1. Alkylations are effected using a base, such as TEA, $K_2CO_3$ or $Cs_2CO_3$, in a solvent such as DMF, THF or $CH_2Cl_2$, with an alkylating agent such as an alkyl or benzyl halide or sulfonate. Acylations are effected using an appropriate carboxylic acid in the presence of a dehydrating agent, for example DEC in the presence of HOBT. Sulfonylation is effected by treating with appropriate sulfonyl chlorides in the presence of a base such as diisopropylethyl amine or $Et_3N$ in a solvent such as $CH_2Cl_2$ or THF.

In the procedure above, the corresponding olefins (compounds wherein A is $=C(R^{11})(R^{12})$) can be prepared from the respective keto compounds by using standard Wittig chemistry known to those skilled in the art.

Reactive groups not involved in the above processes can be protected during the reactions with conventional protecting groups which can be removed by standard procedures after the reaction. The following Table 1 shows some typical protecting groups:

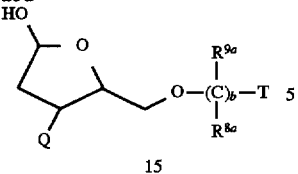

15

The lactol is then reacted with an amine ZH as described in Procedure A, Step 4, to give the amino alcohol 6.

When $R^{20}$ is diarylalkylsilyl, compound 4 (derived from 1E) taken through the same steps (steps1 to 4), is converted to compound 16, which is desilylated by treatment with fluoride ion, preferably TBAF, to give oxime alcohol 17.

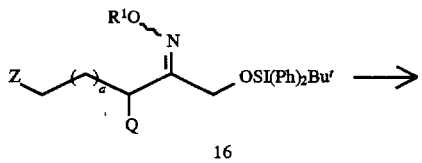

16

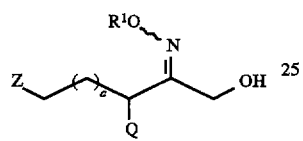

17

Step 5:

Oxime alcohol 17 can be alkylated, acylated, or reacted with isocyanates to obtain ether or carbamate compounds of formula 1. Alkylations are effected using a base, such as NaH, $K_2CO_3$ or $Cs_2CO_3$, in a solvent such as DMF, THF or $CH_2Cl_2$, with an alkylating agent such as an alkyl or benzyl halide or sulfonate. Acylations are effected using an appropriate carboxylic acid in the presence of a dehydrating agent, for example DEC in the presence of HOBT.

Procedure C:

Compounds of formula I wherein A is an oxime derivative and X is an amide or urea are prepared by oxidation of an oxime alcohol and reaction of the resultant aldehyde with an amine, followed by alkylation, acylation, sulfonation or reaction with an isocyanate as shown below:

Step 1:

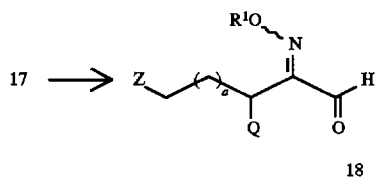

18

TABLE 1

| Group to be Protected | Group to be Protected and Protecting Group |
|---|---|
| —COOH | —COOalkyl, —COObenzyl, —COOphenyl |
| \NH/ | \NCOalkyl/, \NCObenzyl/, \NCOphenyl/, \NCH₂OCH₂CH₂Si(CH₃)₃/, \NC(O)OC(CH₃)₃/, \N-benzyl/, \NSi(CH₃)₃/, \NSi(CH₃)(C(CH₃)₃)(CH₃)/ |
| —NH₂ | succinimide (—N with two C=O) |
| OH— | —OCH₃, —OCH₂OCH₃, —OSi(CH₃)₃, —OSi(CH₃)(C(CH₃)₃)(CH₃), —OSi(Ph)(C(CH₃)₃)(Ph) or —OCH₂phenyl |

Compounds of formula I have been found to be antagonists of NK₁ and/or NK₂ and/or NK₃ receptors, and am therefore useful in treating conditions caused or aggravated by the activity of said receptors.

The present invention also relates to a pharmaceutical composition comprising a compound of formula I and a pharmaceutically acceptable carrier. Compounds of this invention can be administered in conventional oral dosage forms such as capsules, tablets, powders, cachets, suspensions or solutions, or in injectable dosage forms such as solutions, suspensions, or powders for reconstitution. The pharmaceutical compositions can be prepared with conventional excipients and additives, using well known pharmaceutical formulation techniques. Pharmaceutically acceptable excipients and additives include non-toxic and chemically compatibile fillers, binders, disintegrants, buffers, preservatives, anti-oxidants, lubricants, flavorings, thickeners, coloring agents, emulsifiers and the like.

The daily dose of a compound of formula I for treating asthma, cough, bronchspasm, inflammatory diseases, migraine, nociception and gastrointestinal disorders is about 0.1 mg to about 20 mg/kg of body weight per day, preferably about 0.5 to about 15 mg/kg. For an average body weight of 70 kg, the dosage range is therefore from about 1 to about 1500 mg of drug per day, preferably about 50 to about 200 mg, more preferably about 50 to about 500 mg/kg per day, given in a single dose or 2–4 divided doses. The exact dose, however, is determined by the attending clinician and is dependent on the potency of the compound administered, the age, weight, condition and response of the patient.

Following are examples of preparing starting materials and compounds of formula I. As used herein, Me is methyl, Bu is butyl, Br is bromo, Ac is acetyl, Et is ethyl and Ph is phenyl.

Preparation 1

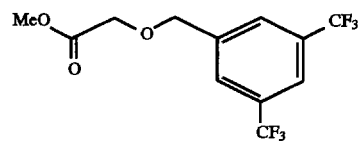

1

Treat methyl glycolate (1.4 g, 0.015 mole) in 50 ml anhydrous THF at 0° C. with sodium hydride (0.65 g, 0.0165 mole). Stir the mixture for 0.5 h and add 3,5-bis trifluoromethyl benzyl bromide (5 g, 0.0165 mole). Allow the mixture to warm to room temp and stir for an additional 10 h. Quench the reaction with CH₃OH (5 mL). Wash with water (3×100 mL) and brine (2×100 mL), separate the organics, dry over MgSO₄, filter, and concentrate under vacuum to obtain a crude oil. Purify by silica gel chromatography (10%EtOAc/Hexane) to obtain pure product (4.2 g).

Preparation 2

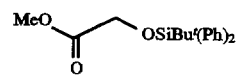

2

Treat methyl glycolate (14 g, 0.15 mole) in 200 ml CH₂Cl₂ with Et₃N (23 mL, 0.165 mole), dimethylaminopyridine (3 g, 0.03 mole), and t-butyldiphenyl silylchloride (46 g, 0.165 mole). Stir the mixture for 24 h and then dilute with 200 mL CH₂Cl₂. Wash with water (3×100 mL) and brine (2×100 mL), separate the organics, dry over MgSO₄, filter, and concentrate under vacuum to obtain a crude oil. Purify by silica gel chromatography (hexane as the elutant) to obtain pure product (46 g).

Preparation 3

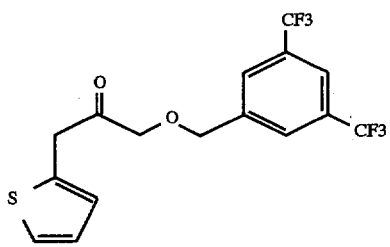

Treat a solution of 2-thiopheneaceticacid (1.6 g, 11.2 mmole) in anhydrous THF (100 mL, −78° C.) with lithium-hexadimethylsilazide (24.5 mmole, 1M THF soln.). Warm the solution to 0° C. over a period of 2 h, then cool to −78° C. and add ethyl [[3,5-bis(trifluoromethyl)phenyl]-methoxy]-acetate (3.55 g, 11.2 mmole) dropwise as a THF solution (10 mL). Stir the resulting mixture for 4 h and allow the temperature to warm to 0° C. Quench the reaction with 1 ml HOAc and stir for 4 h. Dilute the reaction with EtOAc (100 mL), wash the organics with water (2×50 mL) and brine (1×50 mL), dry (Na₂SO₄) and concentrate to obtain 3.4 g of crude product. Purify by silica gel chromatography (3:7 Et₂O:hexane ) to give the title compound, 2.8 g (7.3 mmole, 65.4%) as a colorless foam. MS: (Cl+/CH4) (M+H⁺) 383.

Preparation 4

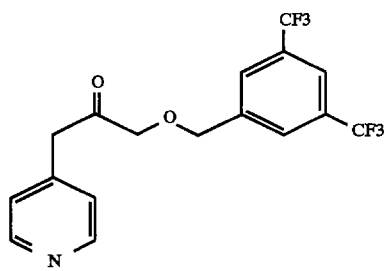

Treat a solution of 4-picoline (1.42 g, 15 mmole) in anhydrous THF (50 mL, −10° C.) with phenyllithium (15 mmole, 8.3 mL cyclohexane:Et₂O) and stir for 1 h at 0° C. Cool the solution to −78° C. and add the product of Example 47, Step 1 (5.27 g, 15 mmole) dropwise as a THF solution (10 mL). Stir the resulting mixture for 4 h (−78° C. to 0° C.) and quench with saturated aqueous NH₄Cl (10 mL). Extract with EtOAc (100 mL), wash with water (2×50 mL), brine (50 mL), dry (Na₂SO₄), and concentrate. Purify by silica gel column chromatography (8:2 EtOAc:hexane) to obtain the title compound. (2.5 g, 44%). MS: (Cl+/CH4) (M+H⁺) 378.

Using a similar procedure with the appropriate heteroaryl acid or heteroaryl methyl compound and corresponding methyl ester, the following compounds were prepared, wherein Q and T are as defined in the table:

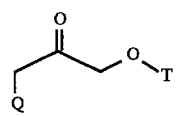

| Prep | Q | T | Physical Data |
|---|---|---|---|
| 4A | 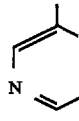 | —CH₂Ph(CF₃)₂ | MS (Cl CH4 + M + H⁺): 379 |
| 4B | 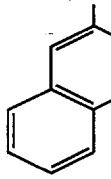 | —CH₂Ph(CF₃)₂ | MS (Cl CH4 + M + H⁺): 427 |
| 4C | 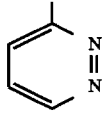 | —CH₂Ph(CF₃)₂ | MS (Cl CH4 + M + H⁺): 379 |
| 4D | 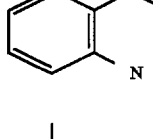 | —CH₂Ph(CF₃)₂ | MS (Cl CH4 + M + H⁺): 428 |
| 4E | 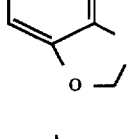 | —CH₂Ph(CF₃)₂ | MS (Cl CH4 + M + H⁺): 421 |
| 4F | 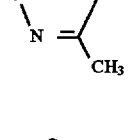 | —CH₂Ph(CF₃)₂ | MS (Cl CH4 + M + H⁺): 382 |
| 4G | 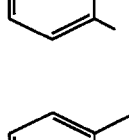 | —CH₂Ph(CF₃)₂ | MS (Cl CH4 + M + H⁺): 433 |
| 4H | 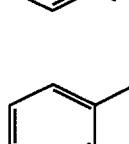 | —Si(Ph)₂But | MS (FAB M + H⁺): 458 |
| 4J |  | —Si(Ph)₂But | MS (FAB M + H⁺): 442 |

Preparation 5

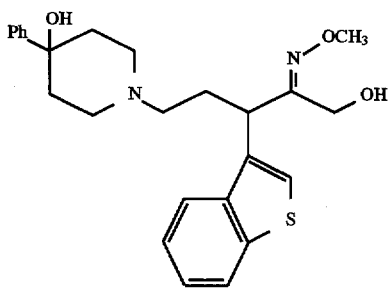

Step 1: The ketone of Preparation 4H is taken through steps 1 to 4 of Example 1.

Step 2: Treat the product of Step 1 (6.3 g, 0.009 mole) in 50 ml anhydrous THF with tetrabutyl ammonium fluoride (0.01 mole). Stir the mixture at room temperature for 24 h and then dilute with 100 mL EtOAc. Wash with water (2×50 mL) and brine (2×50 mL), separate the organics and dry over MgSO₄, filter, and concentrate under vacuum to obtain a crude oil. Purify by silica gel chromatography (1.5% ammonia saturated CH₃OH/3:1 hexane:EtOAc) to obtain the title compound (4.1 g). MS: (FAB ⁺M+H⁺)=439.2.

Preparation 6

Substituted piperidines—Method A

Step 1:

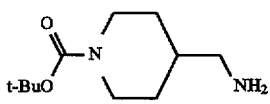

Dissolve 4-aminomethyl-piperidine (30.00 g, 0.263 mol) in CH₃OH (500 mL), cool to −30° C. under N₂, add di-t-butyl dicarbonate (38.23 g, 0.175 mol) in CH₃OH (100 mL) dropwise, warm slowly to 23° C. and stir for 16 h. Concentrate, add CH₂Cl₂ (700 mL), wash with saturated aqueous NaCl (2×200 mL), dry organic solution (MgSO₄), filter and concentrate to give 36.80 g of a 86:14 mixture of the title compound and 1,1-dimethyl-4-[(1,1-dimethylethyloxycarbonyl)methyl]-1-piperidinecarboxylate.

Step 2A:

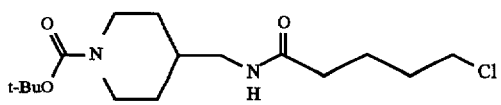

Dissolve the product (19.64 g, 0.0916 mol, 22.84 g of the mixture) of Step 1 in dry CH₂Cl₂ (350 mL) and cool to 0° C. under N₂. Add pyridine (10.87 g, 11.1 mL, 0.137 mol) then chlorovaleryl chloride (15.63 g, 13.0 mL, 0.101 mol), warm slowly to 23° C. and stir for 16 h. Add saturated aqueous NH₄Cl (300 mL), separate layers and extract with CH₂Cl₂ (2×250 mL). Dry combined organic extracts (MgSO₄), filter and concentrate. Purify by chromatography (1000 mL of flash silica gel; eluant: 1:1 EtOAc:hexane, then EtOAc). Combine appropriate fractions and concentrate to give 25.36 g (0.0762 mol, 84%) as a colorless oil. MS (Cl/CH₄): m/e 333 (M+1)

Step 2B:

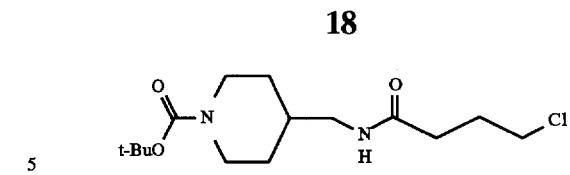

Treat the product of Step 1 in a procedure similar to that described for Step. 2A, using chlorobutryl chloride. MS (FAB): m/e 319 (M+1)

Step 3:

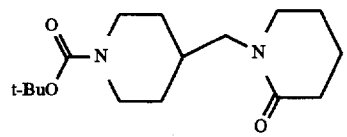

Prep. 6A:

Wash NaH (3.84 g, 0.160 mol, 6.40 g of 60 wt %) with hexane (25 mL), suspend in dry THF (150 mL) and cool to 0° C. under N₂. Add the product (25.35 g, 0.0762 mol) of Step. 2A in dry THF (150 mL) dropwise. Stir at 23° C. for 30 mins, reflux for 6 h, and stir at 23° C. for 16 h. Cool to 0° C. and add water (150 mL) and 1N HCl (150 mL). Concentrate and extract with EtOAc (3×200 mL). Wash combined organic extracts with saturated aqueous NaCl, dry (MgSO₄), filter and concentrate. Purify by chromatography (600 mL of flash silica gel; eluant: 5% CH₃OH—CH₂Cl₂). Combine appropriate fractions and concentrate to give 21.62 g (0.0729 mol, 96%) of the title compound as a yellow oil. MS (FAB): m/e 297 (M+1)

Prep. 6B:

Treat the product of Step 2B in a procedure similar to that described for Prep. 6A. MS (FAB): m/e 283 (M+1).

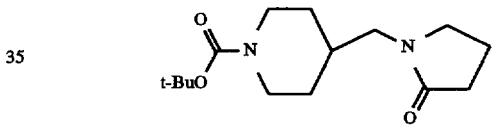

Prep. 6C:

Combine the product (1.50 g, 5.06 mmol) of Prep. 6A and Lawesson reagent (1.13 g, 2.78 mmol) in dry THF (20 mL) under N₂. Stir at 23° C. for 20 h. Concentrate and purify by chromatography (200 mL of flash silica gel; eluant: 1:3 EtOAc:hexane, 1:2 EtOAc:hexane, then 1:1 EtOAc:hexane). Combine appropriate fractions and concentrate to give 1.30 g (4.16 mmol, 82%) as a green oil. MS (FAB): m/e 313 (M+1).

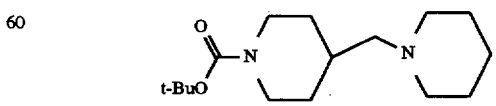

Prep. 6D:

Dissolve the product (2.50 g, 8.43 mmol) of Prep. 6A in dry THF (30 mL), add borane-DMS (16.9 mL of 2.0M in THF, 33.74 mmol) and reflux for 20 h. Cool to 0° C. and add CH₃OH (20 mL). Concentrate, add EtOH (50 mL) and K₂CO₃ (4.66 g, 33.74 mmol). Reflux for 4 h and cool to 23° C. Add water (100 mL), concentrate and extract with CH₂Cl₂ (4×50 mL). Dry combined organic extracts (MgSO₄), filter and concentrate. Purify by chromatography (200 mL of flash silica gel; eluant: 7% CH₃OH—CH₂Cl₂). Combine appropriate fractions and concentrate to give 1.72 g (6.09 mmol, 72%) of the title compound as a colorless oil. MS (FAB): m/e 283 (M+1).

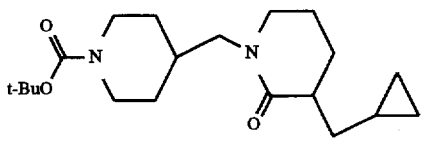

Prep. 6E:

Dissolve the product (1.50 g, 5.06 mmol) of Prep. 6A in dry THF (20 mL) and cool to −78° C. under N₂. Add [(CH₃)₃Si]₂NLi (5.5 mL of 1.0M in THF, 5.5 mmol) and stir at −78° C. for 1 h. Add bromomethylcyclopropane (0.820 g, 0.59 mL, 6.07 mmol), warm slowly to 23° C. and stir for 16 h. Add saturated aqueous NH₄Cl (40 mL), extract with EtOAc (3×30 mL), wash combined organic extracts with saturated aqueous NaCl, dry (MgSO₄), filter and concentrate. Purify by chromatography (175 mL of flash silica gel; eluant: 2% CH₃OH—CH₂Cl₂ then 4% CH₃OH—CH₂Cl₂). Combine appropriate fractions and concentrate to give 0.93 g (2.65 mmol, 53%) of the title compound as a colorless oil. MS (FAB): m/e 351 (M+1)

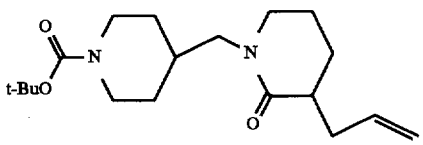

Prep. 6F:

Treat the product of Prep. 6A in a procedure similar to that described for Prep. 6G, using allyl bromide. MS (Cl/CH₄): m/e 337 (M+1).

Step 3: Separately dissolve the products of Prep. 6A to 6H in CH₂Cl₂, add trifluoroacetic acid and stir at 23° C. for 4 h. Concentrate, add 1N NaOH, extract with CH₂Cl₂, dry the combined organic extracts (MgSO₄), filter and concentrate to obtain the corresponding substituted piperidines:

| Prep. | Substituted Piperidine | Data |
|---|---|---|
| 6-1 | | MS(Cl/CH₄): m/e 197(M+1) |
| 6-2 | | MS(Cl/CH₄): m/e 183(M+1) |
| 6-3 | | MS(Cl/CH₄): m/e 213(M+1) |
| 6-4 | | MS(Cl/ isobutane): m/e 183(M+1) |
| 6-5 | | MS(Cl/CH₄): m/e 251(M+1) |
| 6-6 | | MS(Cl/CH₄): m/e 237(M+1) |

Preparation 7

Substituted piperidines—Method B

Step 1:

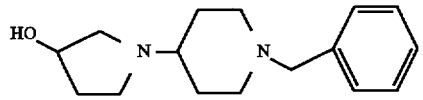

Prep. 7A:

Combine 1-benzyl-4-piperidone (2.00 g, 10.6 mmol) and 3-pyrrolinol (0.92 g, 10.6 mmol) in titanium isopropoxide (3.75 g, 3.9 mL, 13.2 mmol) and dry CH₂Cl₂ (4 mL). Stir at 23° C. under N₂ for 5 h. Add EtOH (30 mL) and NaCNBH₃ (0.66 g, 10.6 mmol) and stir for 16 h. Add water (50 mL) and CH₂Cl₂ (50 mL), filter through celite, separate filtrate layers and extract with CH₂Cl₂ (2×50 mL). Wash combined organic extracts with saturated aqueous NaHCO₃, dry (MgSO₄), filter and concentrate. Purify by chromatography (150 mL of flash silica gel; eluant: 10% CH₃OH with NH₃—CH₂Cl₂, 15% CH₃OH with NH₃—CH₂Cl₂, then 20% CH₃OH with NH₃—CH₂Cl₂.) Combine appropriate fractions and concentrate to give 1.88 g (7.22 mmol, 68%) as a colorless oil. MS (Cl/CH₄): m/e 261 (M+1).

Using the procedure of Prep. 7A and the appropriate amine, prepare Preps. 7B and 7C:

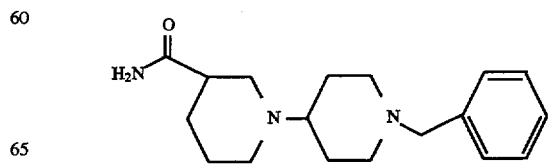

Prep. 7B: MS (FAB): m/e 302 (M+1)

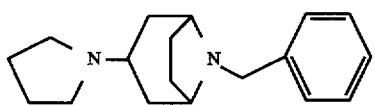

Prep. 7C: MS (Cl/CH₄): m/e 271 (M+1),

Step 2: Separately treat each of Preps. 7A, 7B and 7C with Pd/C catalyst in CH₃OH and formic acid at 23° C. under N₂ for 16 h. Filter each mixture through celite, washing with CH₃OH, concentrate the filtrates, add 1.0N NaOH and extract with 1:4 EtOH:CH₂Cl₂, dry, filter and concentrate to obtain Preps. 7-1, 7-2 and 7-3:

| Prep. | Substituted Piperidine | Data |
|---|---|---|
| 7-1 | | MS(Cl/CH₄): m/e 171 (M + 1) m.p. 138–140° C. |
| 7-2 | | MS(Cl/CH₄): m/e 212 (M + 1) |
| 7-3 | | MS(Cl/CH₄): m/e 181 (M + 1) |

Preparation 8

Substituted Piperidines—Method C

Step 1: Using 1,1-dimethyethyl 4-formyl-piperidinecarboxylate and the appropriate amine in a reductive amination procedure similar to that described in Example 42, Step 9, Preparations 8A, 8B and 8C are prepared:

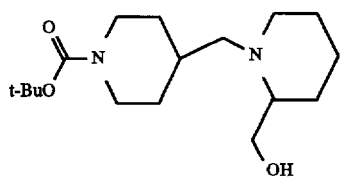

Prep. 8A: MS(Cl/isobutane): m/e313 (M+1)

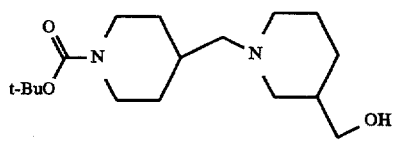

Prep. 8B: MS(Cl/CH₄):m/e313 (M+1)

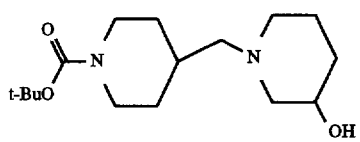

Prep. 8C: MS(FAB):m/e299 (M+1)

Step 2: Using the procedure described in Preparation 6, Step 3, prepare the following compounds:

| Prep. | Substituted Piperidine | Data |
|---|---|---|
| 8-1 | | MS(FAB: m/e 213 (M + 1) |
| 8-2 | | MS(Cl/CH₄):m/e213 (M + 1) |
| 8-3 | | MS(Cl/CH₄):m/e199 (M + 1) |

Preparation 9

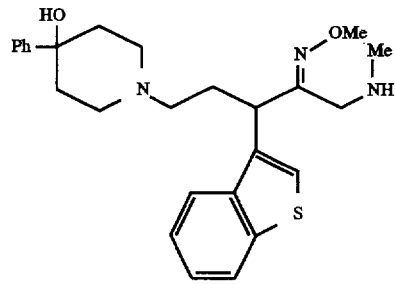

Dissolve the product of Preparation 5 (0.146 g, 0.33 mmole) and o-iodoxybenzoic acid (0.186 g) in 10 mL anhydrous DMSO and add dropwise trifluoroacetic acid as a 1 mL THF solution. Stir the mixture for 4 h. Neutralize the reaction with aqueous solution of Na₂CO₃ (5 mL). Dilute the reaction with 30 mL EtOAc. Separate the organics and wash with 2×10 mL water and 2×10 mL brine. Dry over MgSO₄ and concentrate under vacuum. Treat the crude aldehyde product in 10 mL anhydrous toluene with methyl amine (0.66 mmole). Stir for 2 h and then remove the solvent under vacuum. Redissolve in 10 mL trifluoroethanol and treat with sodium cyanoborohydride (0.041 g, 0.66 mmole). Stir the resulting mixture for 10 h and then quench the reaction with 2 ml water. Dilute the reaction with EtOAc (50 mL) and wash the organics with water (2×25 mL) and brine (1×25 mL). Dry (Na₂SO₄) and concentrate to obtain crude product. Purify by silica gel preparatory plate chromatography (20% ammonia saturated CH₃OH/3:1 hexane:EtOAc) to give the title compound, 0.09 g. MS: (EI M+H⁺)=452.1.

Example 1

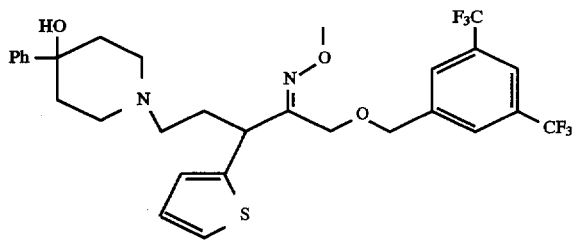

Step 1: Dissolve the product of Preparation 3 (2.6 g, 0.0068 mole) in 30 mL anhydrous THF, cool to −78° C. and add dropwise sodium hexadimethyl silazide (0.0075 mole ) as 1M THF solution. Stir the mixture for 0.5 h at −78° C. Treat the resulting yellow solution with N,N-methyl methoxy iodoacetamide (0.0068 mole) as a 5 mL THF solution. Warm the reaction to 0° C. over 4h and then quench with an aqueous solution of $NH_4Cl$ (5 mL). Dilute the reaction with 100 mL EtOAc. Separate the organics and wash with 2×50 mL water and 2×50 mL brine. Dry over $MgSO_4$ and concentrate under vacuum. Purify the crude by flash silica gel chromatography eluting with 10% EtOAc/hexane to obtain 1.6 g of pure product. MS:EI $M^+$=422.

Step 2: Stir a mixture of the product of step 1 (0.5 g, 0.00105 mole), methoxyl amine hydrochloride (0.52 g, 0.0045 mole) and NaOAc (0.42 g) in 15 mL EtOH:water (5:1) for 20 h. Remove the solvent under vacuum, redissolve the crude in 50 mL EtOAc and wash with 2×50 mL water. Dry the organics and remove the solvent under vacuum. Purify the crude by silica gel flash chromatography, eluting with 20% EtOAc/hexane to obtain two isomeric oximes. Yield of isomer A: 0.33 g; yield of isomer B :0.05 g. MS:isomer A FAB (M+H)+ 513.2; MS:isomer B FAB (M+H)+513.2.

Step 3: Dissolve the major isomer from step 2 (0.65 g, 0.00127 moles) in 20 mL anhydrous THF and cool to −78° C. Add dropwise diisobutylaluminium hydride (0.0045 mole) as 1M hexane solution. Monitor the reaction by drawing samples at intervals for presence of starting material (about 1 h). Quench the reaction at −78° C. by adding a saturated solution of $Na_2SO_4$. Warm the reaction with vigorous stirring (2 h) and remove the precipitated aluminum salts by filtration. Wash the collected solids with 2×50 mL $Et_2O$. Combine the filtrates and concentrate under vacuum.

Step 4: Redissolve the crude aldehyde of step 3 in trifluoroethanol (10 mL) and add phenyl hydroxy piperidine (0.15 g, 0.0008 mole) and powdered 3A molecular sieves (1 g). After stirring for 0.5 h, add sodium cyanoborohydride (0.002 mole) and continue stirring for 20 h. Dilute the reaction with $Et_2O$ (100 mL), filter off the molecular sieves and remove the solvent under vacuum. Purify by flash silica gel chromatography eluting with 1% ammonia saturated $CH_3OH$/3:1 hexane:EtOAc. Yield: 0.04 g isomer A. MS: $(FAB^+M+H^+)$=615.

Example 2

Starting with the appropriate ketone from Preparation 4 and using the corresponding product of Step 3 of Example 1 and the appropriate amines from above (Preparations 6–8) in the procedure of Example 1, the following compounds are prepared:

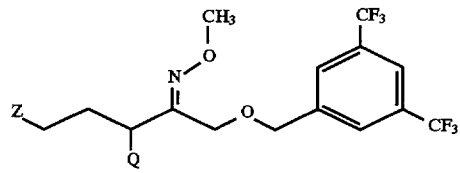

| Ex. | Z | Q | Isomer | Physical Data |
|---|---|---|---|---|
| 2A | H₂NOC-[4-phenylpiperidine]-N— | 2-thienyl | Z | MS(FAB M + H⁺): 642 |
| 2B | Me—N[piperazine]N— | 2-thienyl | Z | MS(FAB M + H⁺): 538 |
| 2C | HO-[4-phenylpiperidine]-N— | pyrimidinyl | Z | MS(FAB M + H⁺): 611.2 |

-continued

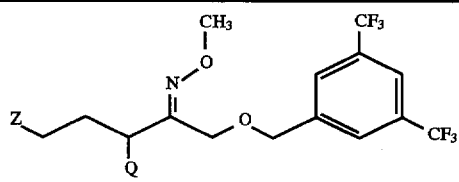

| Ex. | Z | Q | Isomer | Physical Data |
|---|---|---|---|---|
| 2D | (butyrolactam-N-CH2-piperidine-N—) | 3-methylpyrazin-2-yl | E/Z mixture | MS(FAB M + H+): 616.4 |
| 2E | 4-hydroxy-4-phenylpiperidin-N— | 3-methylpyridazin-yl | E/Z mixture | MS(FAB M + H+): 611.0 |
| 2F | 4-hydroxy-4-phenylpiperidin-N— | 4-methylquinolin-yl | Z | MS(FAB M + H+): 660.0 |
| 2G | (butyrolactam-N—) | 4-methylquinolin-yl | Z | MS(FAB M + H+): 650.9 |
| 2H | 4-hydroxy-4-phenylpiperidin-N— | 3-methyl-5-methylisoxazolyl | E/Z mixture | MS(FAB M + H+): 614.0 |
| 2I | (butyrolactam-N—) | 3-methyl-5-methylisoxazolyl | E/Z mixture | MS(FAB M + H+): 605.0 |
| 2J | 4-hydroxy-4-phenylpiperidin-N— | 2,3-dihydrobenzo[1,4]dioxin-yl | E/Z mixture | MS(FAB M + H+): 653 |
| 2K | 4-hydroxy-4-phenylpiperidin-N— | benzothiophen-3-yl | E/Z mixture | MS(FAB M + H+): 665.3 |

Example 3

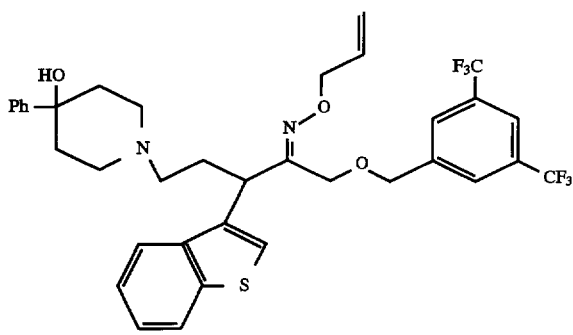

Prepare the allyl oxime ether of the product of Example 2K, using a procedure similar to that used in Example 1, employing O-allylhydroxyl-amine HCl as the alkoxyl amine. MS: FAB (M+H+): 690.9.

Example 4

Using the procedures described below, compounds of the following structural formula were prepared, wherein the definitions of $R^1$ are shown in the following table:

| Ex. | $R^1$ | MS Found FAB(M + H⁺) |
|---|---|---|
| 4A | —H | 651.2 |
| 4B | —CH₂CN | 690.6 |
| 4C | N-OH, NH₂ (structure) | 723.6 |
| 4D | —CH₂CH₂OH | 695.6 |
| 4E | —CH₃ | 665.5 |

Example 4A

Treat a solution of the product of Example 3 (367 mg, 0.53 mmol) in 80% aqueous EtOH with Pd(PPh₃)₄ (60 mg, 0.053 mmol, 0.05 eq) and triethylammoniumformate (3 mL of 1M solution in THF, 5 eq) and stir at reflux for 4 h. Cool, concentrate and purify by silica gel chromatography (2.5× 16.5 cm; CH2CL2/Hex 8:2 w/6% NH₃/MeOH) to give 150 mg of the product as a film.

Example 4B

Treat a solution of Example 4A (93 mg, 0.143 mmol) in dry DMF (10 mL) at 0° C. with 60% NaH in mineral oil (7 mg), stir for 40 min and treat with bromo acetonitrile 0.034 g. Stir for 30 min, pour into EtOAc (250 mL)/half saturated NaHCO₃ (200 mL) and extract. Wash the organic layer with water (2×100 mL), then brine (10 mL) and dry over Na₂SO₄. Purify the crude mixture by silica gel chromatography (4×15 cm; hex/EtOAc 1:1 w/2% NEt₃) to give 30 mg of the pure product as an oil.

Example 4C

Treat a suspension of H₂NOH.HCl (0.14 mmol, 5 eq) in ethanol with KOH in MeOH (680 µL, 0.68 mmol, 5 eq), sonicate for 5 min and then add to a solution of Example 4B (24 mg, 0.035 mmol) in ethanol (5 mL). Heat for 2.5 h at 60° C., filter, concentrate in vacuo and purify by silica gel chromatography (2.5×14 cm; CH₂Cl₂/MeOH (NH₃) 95:5) to give 9 mg of the product.

Example 4D

Treat the product of Example 4A (23 mg), in a similar fashion to Example 4B, using 2-bromo-1-(t butyldimethylsiloxy)ethane (10 mg) as the alkyl halide, followed by desilylation (3 h, 23° C.) with 1M TBAF in THF.

Example 4E

Treat the product of Example 4A in a similar fashion to Example 4B using CH₃I as the alkyl halide to obtain the desired product.

Example 5

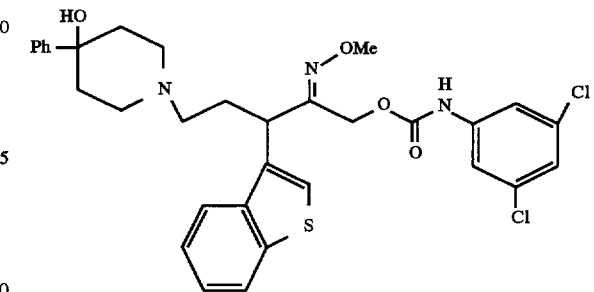

Treat a solution of Preparation 5 (0.1 g, 0.23 mmole) in anhydrous THF (5 mL) with 3,5 dicholorophenyl isocyanate (0.065 g, 0.35 mmole). Stir the resulting mixture for 1 h and then quench the reaction with 2 ml water. Dilute the reaction with EtOAc (50 mL) and wash the organics with water (2×25 mL), brine (1×25 mL). Dry (Na₂SO₄) and concentrate to obtain crude product. Purify by silica gel preparatory plate chromatography (5% ammonia saturated CH₃OH/3:1 hexane:EtOAc) to give the title compound, 0.105 g. MS: (FAB ⁺M+H⁺)=626.3.

Using a similar procedure, prepare compounds of the following formula, wherein the variables are as defined in the table:

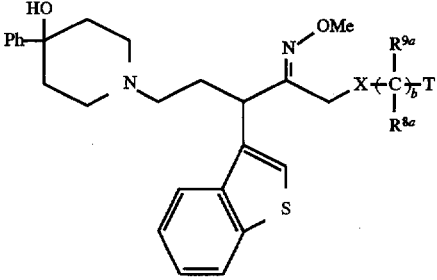

| Ex. | -X(C)ᵦ-T, R⁹ᵃ, R⁸ᵃ | Physical Data |
|---|---|---|
| 5A | 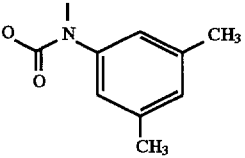 | MS(FAB M + H⁺): 586.4 |
| 5B | 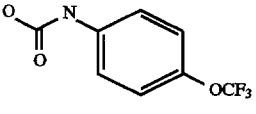 | MS(FAB M + H⁺): 642.4 |
| 5C | 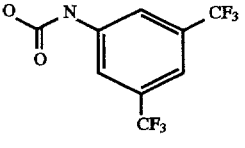 | MS(FAB M + H⁺): 694.4 |
| 5D | 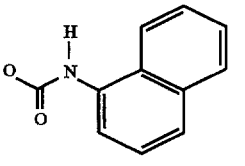 | MS(FAB M + H⁺): 608.4 |
| 5E | 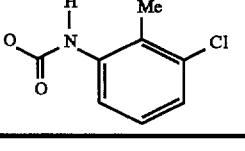 | MS(FAB M + H⁺): 606.9 |

Example 6

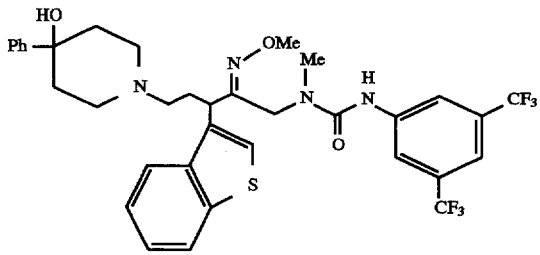

Treat a solution of Preparation 9 (0.1 g, 0.23 mmole) in anhydrous THF (5 mL) with 3,5-bis trifluoromethylphenyl isocyanate (0.065 g, 0.35 mmole). Stir the resulting mixture for 1 h and then quench the reaction with 2 ml water. Dilute the reaction with EtOAc (50 mL) and wash the organics with water (2×25 mL) and brine (1×25 mL). Dry (Na₂SO₄) and concentrate to obtain crude product. Purify by silica gel preparatory plate chromatography (5% ammonia saturated CH₃OH /3:1 hexane:EtOAc) to give the title compound 0.105 g. MS: (FAB ⁺M+H⁺)=706.

Example 7

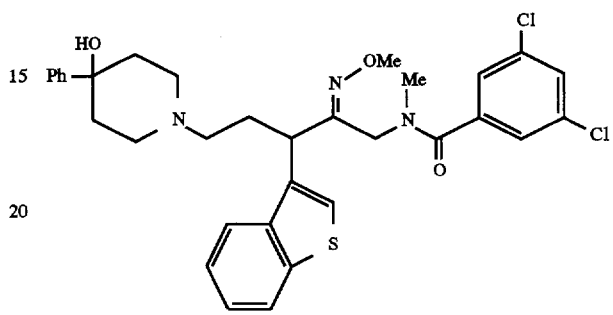

To a CH₂Cl₂ (2 mL) solution containing the product of Preparation 9 (0.05 g, 0.11 mmole), 3,5 dichlorobenzoic acid (0.023 g, 0.13 mmole), and hydroxybenzotriazole (0.0171 g, 0.13 mmole), add 1-(3-dimethylamino-propyl)-3-ethylcarbodiimide hydrochloride (0.025 g, 0.13 mmole). Stir the mixture for 4 h and then dilute with 25 mL CH₂Cl₂. Wash the organics with water (2×25 mL) and brine (1×25 mL). Dry (Na₂SO₄) and concentrate to obtain crude product. Purify by silica gel preparatory plate chromatography (10% ammonia saturated CH₃OH/3:1 hexane:EtOAc) to give the title compound 0.09 g. MS: (EI M+H⁺)=624.2

Using a similar procedure, prepare compounds of the following formula, wherein the variables are as defined in the table:

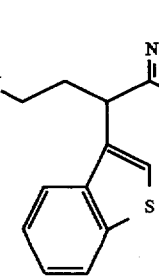

| Ex. | -X(C)ᵦ-T, R⁹ᵃ, R⁸ᵃ | Physical Data |
|---|---|---|
| 7A | 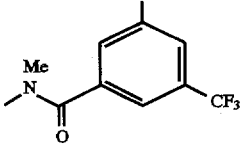 | MS(FAB M + H⁺): 692.3 |

31
-continued

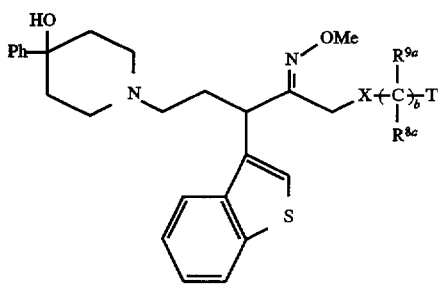

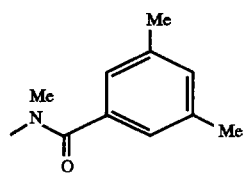

| Ex. | -X(C)T R9a R8a | Physical Data |
|---|---|---|
| 7B | 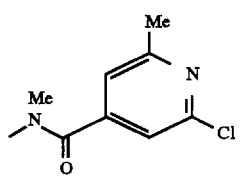 | MS(FAB M + H+): 584.3 |
| 7C | 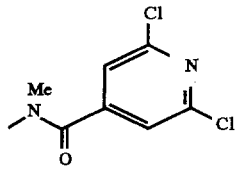 | MS(FAB M + H+): 605.4 |
| 7D | 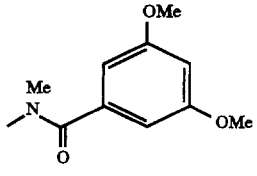 | MS(FAB M + H+): 625.4 |
| 7E | 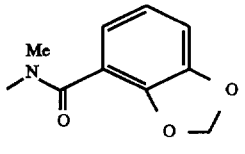 | MS(FAB M + H+): 616.1 |
| 7F | | MS(FAB M + H+): 600.2 |

32
Example 8

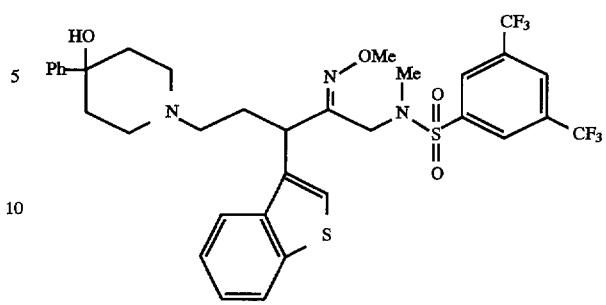

Treat a $CH_2Cl_2$ solution (5 mL) of amine 12 (0.069 g, 0.152 mmole) and diisopropyl ethyl amine (0.04 mL) with 3,5-bis trifluoromethyl-phenylsulfonyl chloride (0.057 g, 0.18 mmole). Stir the mixture for 1 h and then dilute with 25 mL $CH_2Cl_2$. Wash the organics with water (2×25 mL) and brine (1×25 mL). Dry ($Na_2SO_4$) and concentrate to obtain crude product. Purify by silica gel preparatory plate chromatography (10% ammonia saturated $CH_3OH$/3:1 hexane:EtlOAc) to give the title compound, 0.03 g. (FAB +M+H+)=728.7.

Using a similar procedure, prepare compounds of the following formula, wherein the variables are as defined in the table:

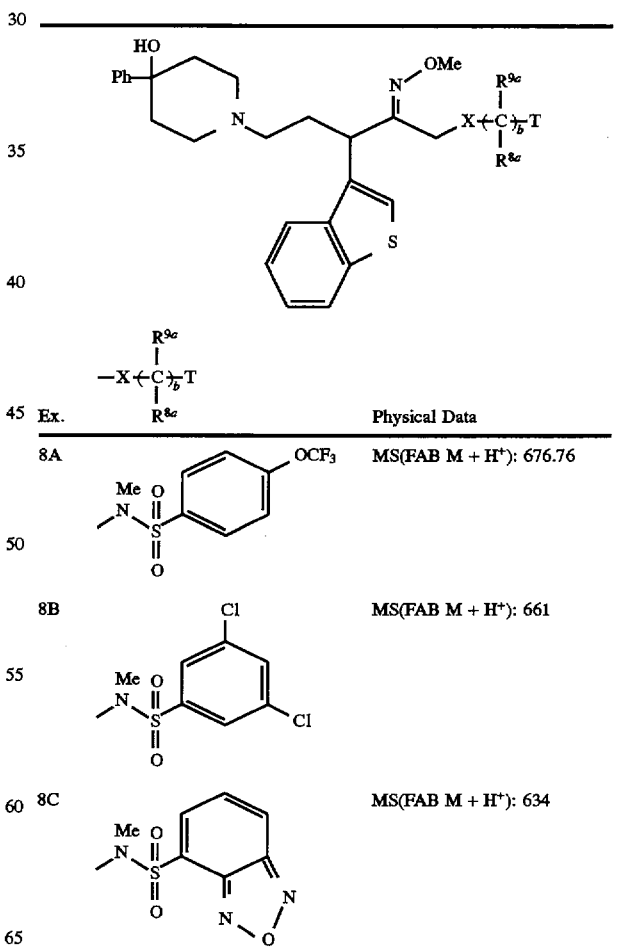

The following formulations exemplify some of the dosage forms of this invention. In each, the term "active compound" refers to a compound of formula I.

EXAMPLE A

Tablets

| No. | Ingredient | mg/tablet | mg/tablet |
|---|---|---|---|
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
|   | Total | 300 | 700 |

Method of Manufacture

Mix Item Nos. 1 and 2 in suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weight on a suitable tablet machine.

EXAMPLE B

Capsules

| No. | Ingredient | mg/tablet | mg/tablet |
|---|---|---|---|
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |
|   | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

EXAMPLE C

Sterile Powder for Injection

| Ingredient | mg/vial | mg/vial |
|---|---|---|
| Active sterile powder | 100 | 500 |

For reconstitution add sterile water for injection or bacteriostatic water for injection.

The in vitro and in vivo activity of the compounds of formula I can be determined by the following procedures.
In vitro procedure to identify $NK_1$ activity Test compounds are evaluated for their ability to inhibit the activity of the $NK_1$ agonist Substance P on the isolated guinea pig vas deferens. Freshly cut vas deferens are removed from male Hartley guinea pigs (230–350 g) and suspended in 25 ml tissue baths containing Kreb's Henseleit solution warmed to 37° C. and constantly aerated with 95% $O_2$ and 5% $CO_2$. Tissues are adjusted to 0.5 g and allowed to equilibrate for a period of 30 minutes. The vas deferens are exposed to an electrical field stimulation (Grass S48 Stimulator) every 60 seconds at an intensity that will cause the tissue to contract 80% of its maximum capacity. All responses are recorded isometrically by means of a Grass force displacement transducer (FT03) and Harvard electronic recorder. Substance P potentiates the electrical field stimulated-induced contractions of the guinea pig vas deferens. In unpaired studies, all tissues (control or drug treated) are exposed to cumulative concentrations of Substance P ($1\times10^{-10}$M–$7\times10^{-7}$M). Single log-concentrations of the test compounds are given to separate tissues and allowed to equilibrate for 30 minutes before a Substance P concentration-response curve is generated. At least 5 separate tissues are used for each control and individual drug-concentration for every drug assay.

Inhibition of the Substance P is demonstrated by a rightward shift of its concentration-response curve. These shifts are used to determine the $pA_2$ value, which is defined as the negative log of the molar concentration of the inhibitor which would require that twice as much agonist be used to elicit a chosen response. This value is used to determine relative antagonist potency.
Isolated Hamster Trachea $NK_2$ Assay General methodology and characterization of hamster trachea responses to neurokinin agonists as providing an $NK_2$ monoreceptor assay is found in C. A. Maggi, et al., Eur. J. Pharmacol. 166 (1989) 435 and J. L. Ellis, et al., J. Pharm. Exp. Ther. 267 (1993) 95.

Continuous isometric tension monitoring is achieved with Grass FT-03 force displacement transducers connected to Buxco Electronics preamplifiers built into a Graphtec Linearcorder Model WR 3310.

Male Charles River LAK:LVG (SYR) hamsters, 100–200 g fed weight, are stunned by a sharp blow to the head, loss of corneal reflex is assured, the hamsters are sacrificed by thoractomy and cutting the heart. Cervical trachea segments are removed to room temperature Krebs buffer, pH 7.4, aerated with 95% $O_2$–5% $CO_2$ gas and cleaned of adhering tissue. The segments are cut into two 3–4 mm long ring segments. Tracheal rings are suspended from transducers and anchored in 15.0 ml water jacketed organ baths by means of stainless steel hooks and 6-0 silk. Baths are filled with Krebs buffer, pH 7.4, maintained at 37° C. and continuously aerated with 95% $O_2$–5% $CO_2$ gas. Tracheal rings are placed under 1.0 g initial tension and allowed a 90 min equilibration period with four 1 µM NKA challenge, wash and recovery cycles at 20 min intervals. 30 min vehicle pretreatment is followed by cumulative additions of rising doses of NKA (3 nM–1 µM final concentration, 5 min intervals between additions). The final NKA response is followed by a 15 min wash and recovery period. 30 min pretreatment with a test compound or its vehicle is followed by cumulative additions of rising doses of NKA (3 nM–10 µM final concentration if necessary, 5 min intervals between additions). The final NKA response is followed by a 1 mM carbachol challenge to obtain a maximal tension response in each tissue.

Tissue responses to NKA am recorded as positive pen displacements over baseline and converted to grams tension by comparison to standard weights. Responses are normalized as a % of the maximal tissue tension. $ED_{50}$'s are calculated for NKA from the control and treated NKA dose responses and compared. Test compounds resulting in an agonist dose ratio >2 at a screening concentration of 1 μM (i.e. $pA_2 \geq =6.0$) are considered actives. Further dose response data is obtained for actives so that an apparent $pA_2$ estimate can be calculated. $pA_2$ is calculated either by estimation of $K_i$ as described by Furchgott (where $pA_2 = -\text{Log } K_i$, R. F. Furchgott, *Pharm. Rev.* 7 [1995]183) or by Shild Plot Analysis (O. Arunlakshana & H. O. Shild, *Br. J. Pharmacol.* 14[1959]48) if the data is sufficient.

Effect of $NK_1$ Antagonists on Substance P-Induced Airway Microvascular Leakage in Guinea Pigs Studies are performed on male Hartley guinea pigs ranging in weight from 400–650 g. The animals are given food and water ad libitum. The animals are anesthetized by intraperitoneal injection of dialurethane (containing 0.1 g/ml diallylbarbituric acid, 0.4 g/ml ethylurea and 0.4 g/ml urethane). The trachea is cannulated just below the larynx and the animals are ventilated ($V_T$=4 ml, f=45 breaths/min) with a Harvard rodent respirator. The jugular vein is cannulated for the injection of drugs.

The Evans blue dye technique (Danko, G. et al., *Pharmacol. Commun.*, 1, 203–209, 1992) is used to measure airway microvascular leakage (AML). Evans blue (30 mg/kg) is injected intravenously, followed 1 min later by i.v. injection of substance P (10 μg/kg). Five min later, the thorax is opended and a blunt-ended 13-guage needle passed into the aorta. An incision is made in the right atrium and blood is expelled by flushing 100 ml of saline through the aortic catheter. The lungs and trachea are removed en-bloc and the trachea and bronchi are then blotted dry with filter paper and weighed. Evans blue is extracted by incubation of the tissue at 37° C. for 18 hr in 2 ml of formamide in stoppered tubes. The absorbance of the formamide extracts of dye is measured at 620 nm. The amount of dye is calculated by interpolation from a standard curve of Evans blue in the range 0.5–10 μg/ml in formamide. The dye concentration is expressed as ng dye per mg tissue wet weight. Test compounds were suspended in cyclodextran vehicle and given i.v. 5 min before substance P.

Measurement of $NK_2$ Activity In Vivo

Male Hartley guinea pigs (400–500 gm) with ad lib. access to food and water are anesthetized with an intraperitoneal injection of 0.9 ml/kg dialurethane (containing 0.1 g/m diallylbarbituric acid, 0.4 g/ml ethylurea and 0.4 g/ml urethane). After induction of a surgical plane of anesthesia, tracheal, esophageal and jugular venous cannulae are implanted to facilitate mechanical respiration, measurement of esophageal pressure and administration of drugs, respectively.

The guinea pigs are placed inside a whole body plethysmograph and the catheters connected to outlet ports in the plethysmograph wall. Airflow is measured using a differential pressure transducer (Validyne, Northridge Calif., model MP45-1, range ±2 $cmH_2O$) which measures the pressure across a wire mesh screen that covers a 1 inch hole in the wall of the plethysmograph. The airflow signal is electrically integrated to a signal proportional to volume. Transpulmonary pressure is measured as the pressure difference between the trachea and the esophagus using a differential pressure transducer (Validyne, Northridge, Calif., model MP45-1, range ±20 cm $H_2O$). The volume, airflow and transpulmonary pressure signals are monitored by means of a pulmonary analysis computer (Buxco Electronics, Sharon, Conn., model 6) and used for the derivation of pulmonary resistance ($R_L$) and dynamic lung compliance ($C_{Dyn}$).

Bronchoconstriction Due to NKA

Increasing iv doses of NKA are administered at half log (0.01–3 μg/kg) intervals allowing recovery to baseline pulmonary mechanics between each dose. Peak bronchoconstriction occurs within 30 seconds after each dose of agonist. The dose response is stopped when $C_{Dyn}$ is reduced 80–90% from baseline. One dose-response to NKA is performed in each animal. Test compounds are suspended in cyclodextran vehicle and given i.v. 5 min before the initiation of the NKA dose response.

For each animal, dose response curves to NKA are constructed by plotting the percent increase in $R_L$ or decrease in $C_{Dyn}$ against log dose of agonist. The doses of NKA that increased $R_L$ by 100% ($R_L100$) or decreased $C_{Dyn}$ by 40% ($C_{Dyn}40$) from baseline values are obtained by log-linear interpolation of the dose response curves.

Neurokinin Receptor Binding Assay(s)

Chinese Hamster ovary (CHO) cells transfected with the coding regions for the human neurokinin 1 (NK1) of the human neurokinin 2 (NK2) receptors are grown in Dulbecco's minimal essential medium supplemented with 10% fetal calf serum, 0.1 mM non-essential amino acids, 2 mM glutamine, 100 units/ml of penicillin and streptomycin, and 0.8 mg of G418/ml at 37° C. in a humidified atmosphere containing 5% $CO_2$.

Cells are detached from T-175 flasks with a sterile solution containing 5 mM EDTA in phosphate buffered saline. Cells are harvested by centrifugation and washed in RPMI media at 40° C. for 5 minutes. The pellet is resuspended in Tris-HCl (pH7.4) containing 1 uM phosphoramidon and 4 ug/ml of chymostatin at a cell density of $30 \times 10^6$ cells/ml. The suspension is then homogenized in a Brinkman Polytron (setting 5) for 30–45 seconds. The homogenate is centrifuged at 800 ×g for 5 min at 4° C. to collect unbroken cells and nuclei. The supernatant is centrifuged in a Sorvall RC5C at 19,000 rpm (44,00 ×g) for 30 min at 4° C. The pellet is resuspended, an aliquot is removed for a protein determination (BCA) and washed again. The resulting pellet is stored at −80° C.

To assay receptor binding, 50 μl of [$^3$H]-Substance P (9-Sar, 11-Met [02]) (specific activity 41 Ci/mmol) (Dupont-NEN) (0.8 nM for the NK-1 assay) or [$^3$H]-Neurokinin A (specific activity 114 Ci/mmole) (Zenca) (1.0 nM for the NK-2 assay) is added to tubes containing buffer (50 mM Tris-HCl (pH 7.4) with 1 mM $MnCl_2$ and 0.2% Bovine Serum Albumin) and either DMSO or test compound. Binding is initiated by the addition of 100 μl of membrane (10–20 μg) containing the human NK-1 or NK-2 receptor in a final volume of 200 μl. After 40 minutes at room temperature, the reaction is stopped by rapid filtration onto Whatman GF/C filters which have been presoaked in 0.3% polyethylenimine. Filters are washed 2 times with 3 ml of 50 mM Tris-HCl (pH7.4). Filters are added to 6 mls of Ready-Safe liquid scintillation cocktail and quantified by liquid scintillation spectrometry in a LKB 1219 RackBeta counter. Non-specific binding is determined by the addition of either 1 μM of CP-99994 (NK-1) or 1 μM SR-48968 (NK-2) (both synthesized by the chemistry department of Schering-Plough Research Institute). $IC_{50}$ values are determined from competition binding curves and Ki values are determined according to Cheng and Prusoff using the experimentally determined value of 0.8 nM for the NK-1 receptor and 2.4 nM for the NK-2 receptor.

$NK_3$ activity is determined by following a procedure similar to that described in the literature, e.g., *Molecular Pharmacol.*, 48 (1995), p. 711–716.

% Inhibition is the difference between the percent of maximum specific binding (MSB) and 100%. The percent of MSB is defined by the following equation, wherein "dpm" is disintegrations per minute:

$$\% MSB = \frac{(\text{dpm of unknown}) - (\text{dbm of nonspecific binding})}{(\text{dpm of total binding}) - (\text{dpm of nonspecific binding})} \times 100$$

It will be recognized that compounds of formula I exhibit $NK_1$, $NK_2$ and/or $NK_3$ antagonist activity to varying degrees, e.g., certain compounds have strong $NK_1$ antagonist activity, but weaker $NK_2$ and $NK_3$ antagonist activity, while others are strong $NK_2$ antagonists, but weaker $NK_1$ and $NK_3$ antagonists. While compounds with approximate equipotency are preferred, it is also within the scope of this invention to use compounds of with unequal $NK_1/NK_2/NK_3$ antagonist activity when clinically appropriate.

Using the test procedures described above, the following data (Ki) were obtained for preferred and/or representative compounds of formula I:

| Ex. | Ki (NK$_1$) (nM) | Ki (NK$_2$) (nM) |
|---|---|---|
| 4D | 1.8 | 23 |
| 7B | 0.65 | 4.5 |

Compounds of the present invention exhibit a range of activity: percent inhibition at a dosage of 1 μM ranges from about 0 to about 100% inhibition of $NK_1$ and/or about 0 to about 100% inhibition of $NK_2$. Preferred are compounds having a Ki≦100 nM for the $NK_1$ receptor. Also preferred are compounds having a Ki≦100 nM for the $NK_2$ receptor. Another group of preferred compounds are those having a Ki≦100 nM for each of the $NK_1$ and $NK_2$ receptors.

We claim:

1. A compound represented by the structural formula

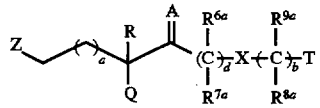

or a pharmaceutically acceptable salt thereof, wherein:

a is 0, 1, 2 or 3;

b and d are independently 0, 1 or 2;

R is H, $C_{1-6}$ alkyl, —OR$^6$ or $C_2$–$C_6$ hydroxyalkyl;

A is =N—OR$^1$, =N—N(R$^2$)(R$^3$), =C(R$^{11}$)(R$^{12}$) or =NR$^{25}$;

X is a bond, —C(O)—, —O—, —NR$^6$—, —S(O)$_e$—, —N(R$^6$)C(O)—, —C(O)N(R$^6$)— —OC(O)NR$^6$—, —OC(=S)NR$^6$—, —N(R$^6$)C(=S)O—, —C(=NOR$^1$)—, —S(O)$_2$N(R$^6$)—, —N(R$^6$)S(O)$_2$—, —N(R$^6$)C(O)O— or —OC(O)—, provided that when d is 0, X is a bond, —C(O)—, —NR$^6$—, —C(O)N(R$^6$)—, —N(R$^6$)C(O)—, —OC(O)NR$^6$—, —C(=NOR$^1$)—, —N(R$^6$)C(=S)O—, —OC(=S)NR$^6$—, —N(R$^6$)S(O)$_2$— or —N(R$^6$)C(O)O—; provided that when A is =C(R$^{11}$)(R$^{12}$) and d is 0, X is not —NR$^6$— or —N(R$^6$)C(O)—; and provided that when A is =NR$^{25}$, d is 0 and X is —NR$^6$— or —N(R$^6$)C(O)—;

T is H, R$^4$-aryl, R$^4$-heterocycloalkyl, R$^4$-heteroaryl, phthalimidyl, R$^4$-cycloalkyl or R$^{10}$-bridged cycloalkyl;

Q is R$^5$-heteroaryl;

R$^1$ is H, $C_{1-6}$ alkyl, —(C(R$^6$)(R$^7$))$_n$—G, —G$^2$, —(C(R$^6$)(R$^7$))$_p$—M— (C(R$^{13}$)(R$^{14}$))$_n$—(C(R$^8$)(R$^9$))$_u$—G, —C(O)N(R$^6$)—(C(R$^{13}$)(R$^{14}$))$_n$—(C(R$^8$)(R$^9$))$_u$—G or —(C(R$^6$)(R$^7$))$_p$—M—(R$^4$-heteroaryl);

R$^2$ and R$^3$ are independently selected from the group consisting of H, $C_{1-6}$ alkyl, —CN, —(C(R$^6$)(R$^7$))$_n$—G, —G$^2$, —C(O)—(C(R$^8$)(R$^9$))$_n$—G and —S(O)$_e$R$^{13}$; or R$^2$ and R$^3$, together with the nitrogen to which they are attached, form a ring of 5 to 6 members, wherein 0, 1 or 2 ring members are selected from the group consisting of —O—, —S— and —N(R$^{19}$)—;

R$^4$ and R$^5$ are independently 1–3 substituents independently selected from the group consisting of H, halogeno, —OR$^6$, —OC(O)R$^6$, —OC(O)N(R$^6$)(R$^7$), —N(R$^6$)(R$^7$), $C_{1-6}$ alkyl, —CF$_3$, —C$_2$F$_5$, —COR$^6$, —CO$_2$R$^6$, —CON(R$^6$)(R$^7$), —S(O)$_e$R$^{13}$, —CN, —OCF$_3$, —NR$^6$CO$_2$R$^{16}$, —NR$^6$COR$^7$, —NR$^8$CON (R$^6$)(R$^7$), R$^{15}$-phenyl, R$^{15}$-benzyl, NO$_2$, —N(R$^6$)S(O)$_2$ R$^{13}$ or —S(O)$_2$N(R$^6$)(R$^7$); or adjacent R$^4$ substituents or adjacent R$^5$ substituents can form a —O—CH$_2$—O— group; and R$^4$ can also be R$^{15}$-heteroaryl;

R$^6$, R$^7$, R$^8$, R$^{6a}$, R$^{7a}$, R$^{8a}$, R$^{13}$ and R$^{14}$ are independently selected from the group consisting of H, $C_{1-6}$ alkyl, $C_2$–$C_6$ hydroxyalkyl, $C_1$–$C_6$ alkoxy-$C_1$–$C_6$ alkyl, R$^{15}$-phenyl, and R$^{15}$-benzyl; or R$^6$ and R$^7$, together with the nitrogen to which they are attached, form a ring of 5 to 6 members, wherein 0, 1 or 2 ring members are selected from the group consisting of —O—, —S— and —N(R$^{19}$)—;

R$^9$ and R$^{9a}$ are independently selected from the group consisting of R$^6$ and —OR$^6$ R$^{10}$ and R$^{10a}$ are independently selected from the group consisting of H and $C_{1-6}$ alkyl;

R$^{11}$ and R$^{12}$ are independently selected from the group consisting of H, $C_1$–$C_6$ alkyl, —CO$_2$R$^6$, —OR$^6$, —C(O)N(R$^6$)(R$^7$), $C_1$–$C_6$ hydroxyalkyl, —(CH$_2$)$_r$—OC(O)R$^6$, —(CH$_2$)$_r$—OC(O)CH=CH$_2$, —(CH$_2$)$_r$—O (CH$_2$)$_s$—CO$_2$R$^6$, —(CH$_2$)$_r$—O—(CH$_2$)$_s$—C(O)N(R$^6$) (R$^7$) and —(CH$_2$)$_r$—N(R$^6$)(R$^7$);

R$^{15}$ is 1 to 3 substituents independently selected from the group consisting of H, $C_1$–$C_6$ alkyl, $C_1$–$C_6$ alkoxy, $C_1$–$C_6$ alkylthio, halogeno, —CF$_3$, —C$_2$F$_5$, —COR$^{10}$, —CO$_2$R$^{10}$, —C(O)N(R$^{10}$)$_2$, —S(O)$_e$R$^{10a}$, —CN, —N(R$^{10}$)COR$^{10}$, —N(R$^{10}$)CON(R$^{10}$)$_2$ and —NO$_2$;

R$^{16}$ is $C_{1-6}$ alkyl, R$^{15}$-phenyl or R$^{15}$-benzyl;

R$^{19}$ is H, $C_1$–$C_6$ alkyl, —C(O)N(R$^{10}$)$_2$, —CO$_2$R$^{10}$, —(C (R$^8$)(R$^9$))$_f$—CO$_2$R$^{10}$ or —(C(R$^8$)(R$^9$))$_u$—C(O)N (R$^{10}$)$_2$;

f, n, p, r and s are independently 1–6;

u is 0–6;

G is selected from the group consisting of H, R$^4$-aryl, R$^4$-heterocycloalkyl, R$^4$-heteroaryl, R$^4$-cycloalkyl, —OR$^6$, —N(R$^6$)(R$^7$), —COR$^6$, —CO$_2$R$^6$, —CON(R$^7$) (R$^9$), —S(O)$_e$R$^{13}$, —NR$^6$CO$_2$R$^{16}$, —NR$^6$COR$^7$, —NR$^8$CON(R$^6$)(R$^7$), —N(R$^6$)S(O)$_2$R$^{13}$, —S(O)$_2$N (R$^6$)(R$^7$), —OC(O)R$^6$, —OC(O)N(R$^6$)(R$^7$), —C(=NOR$^8$)N(R$^6$)(R$^7$), —C(=NR$^{25}$)N(R$^6$)(R$^7$), —N(R$^8$)C(=NR$^{25}$)N(R$^6$)(R$^7$), —CN, —C(O)N(R$^6$) OR$^7$, and —C(O)N(R$^9$)—(R$^4$-heteroaryl), provided that when n is 1 and u is 0, or when R$^9$ is —OR$^6$, G is not —OH or —N(R$^6$)(R$^7$);

M is selected from the group consisting of a double bond, —O—, —N(R$^6$)—, —C(O)—, —C(R$^6$)(OR$^7$)—, —C(R$^8$)(N(R$^6$)(R$^7$))—, —C(=NOR$^6$)N(R$^7$)—, —C(N(R$^6$)(R$^7$))=NO—, —C(=NR$^{25}$)N(R$^6$)—, —C(O)N(R$^9$)—, —N(R$^9$)C(O)—, —C(=S)N(R$^9$)—, —N(R$^9$)C(=S)— and —N(R$^6$)C(O)N(R$^7$)—, provided that when n is 1, G is not OH or —NH(R$^6$); and when p is 2–6, M can also be —N(R$^6$)C(=NR$^{25}$)N (R$^7$)— or —OC(O)N(R$^6$)—;

G$^2$ is R$^4$-aryl, R$^4$-heterocycloalkyl, R$^4$-heteroaryl, R$^4$-cycloalkyl, —COR$^6$, —CO$_2$R$^{16}$, —S(O)$_2$N(R$^6$) (R$^7$) or —CON(R$^6$)(R$^7$);

e is 0, 1 or 2, provided that when e is 1 or 2, $R^{13}$ and $R^{10a}$ are not H;

$R^{25}$ is H, $C_1$-$C_6$ alkyl, —CN, $R^{15}$-phenyl or $R^{15}$-benzyl;

Z is

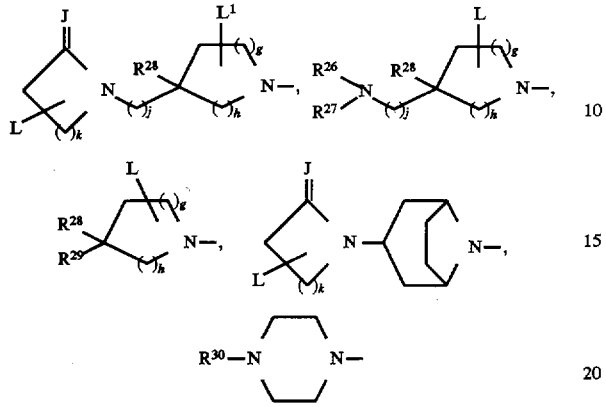

or morpholinyl;

g and j are independently 0–3;

h and k are independently 1–4, provided the sum of h and g is 1–7;

J is two hydrogen atoms, =O, =S, =$NR^9$ or =$NOR^1$;

L and $L^1$ are independently selected from the group consisting of H, $C_1$-$C_6$ alkyl, $C_1$-$C_6$ alkenyl, —$CH_2$-cycloalkyl, $R^{15}$-benzyl, $R^{15}$-heteroaryl, —C(O)$R^6$, —$(CH_2)_m$—$OR^6$, —$(CH_2)_m$—N($R^6$)($R^7$), —$(CH_2)_m$—C(O)—$OR^6$ and —$(CH_2)_m$—C(O)N($R^6$)($R^7$);

m is 0 to 4, provided that when j is 0, m is 1–4;

$R^{26}$ and $R^{27}$ are independently selected from the group consisting of H, $C_1$-$C_6$ alkyl, $R^4$-aryl and $R^4$-heteroaryl; or $R^{26}$ is H, $C_1$-$C_6$ alkyl, $R^4$-aryl or $R^4$-heteroaryl, and $R^{27}$ is —C(O)$R^6$, —C(O)—N($R^6$)($R^7$), —C(O)($R^4$-aryl), —C(O)($R^4$-heteroaryl), —$SO_2R^{13}$ or —$SO_2$—($R^4$-aryl);

$R^{28}$ is H, —(C($R^6$)($R^{19}$))$_t$—G, —(C($R^6$)($R^7$))$_v$—$G^2$ or —$NO_2$;

t and v are 0, 1, 2 or 3, provided that when j is 0, t is 1, 2 or 3;

$R^{29}$ is H, $C_1$-$C_6$ alkyl, —C($R^{10}$)$_2$S(O)$_e$$R^6$, $R^4$-phenyl or $R^4$-heteroaryl;

$R^{30}$ is H, $C_1$-$C_6$ alkyl, $R^4$-cycloalkyl, —(C($R^{10}$)$_2$)$_w$—($R^4$-phenyl), —(C($R^{10}$)$_2$)$_w$—($R^4$-heteroaryl), —C(O)$R^6$, —C(O)O$R^6$, —C(O)N($R^6$)($R^7$),

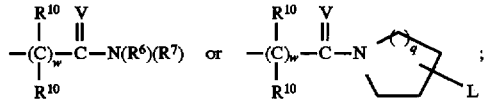

w is 0, 1, 2, or 3;

V is =O, =S or =$NR^6$; and q is 0–4.

2. A compound of claim 1 wherein X is —O—, —C(O)—, a bond, —$NR^6$—, —S(O)$_e$—, —N($R^6$)C(O)—, —C(O)$NR^6$, —OC(O)$NR^6$— or —C(=$NOR^1$)—.

3. A compound of claim 1 wherein T is $R^4$-aryl, $R^4$-heteroaryl, $R^4$-cycloalkyl or $R^{10}$-bridged cycloalkyl.

4. A compound of claim 1 wherein Q is $R^5$-heteroaryl wherein $R^5$ is H.

5. A compound of claim 1 wherein $R^{6a}$, $R^{7a}$, $R^{8a}$ and $R^{9a}$ are independently selected from the group consisting of H, hydroxyalkyl and alkoxyalkyl.

6. A compound of claim 1 wherein Z is

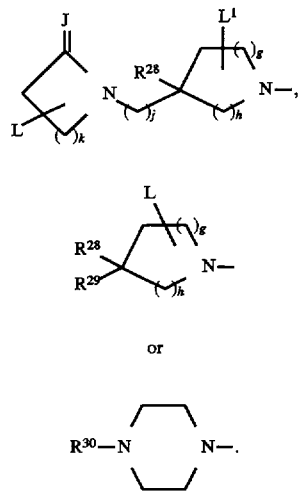

7. A compound of claim 1 wherein X is —O—, —C(O)—, a bond, —$NR^6$—, —S(O)$_e$—, —N($R^6$)C(O)—, —C(O)$NR^6$, —OC(O)$NR^6$— or —C(=$NOR^1$)—; T is $R^4$-aryl, $R^4$-heteroaryl, $R^4$-cycloalkyl or $R^{10}$-bridged cycloalkyl; $R^{6a}$, $R^{7a}$, $R^{8a}$ and $R^{9a}$ are independently selected from the group consisting of H, hydroxyalkyl and alkoxyalkyl; and Z is

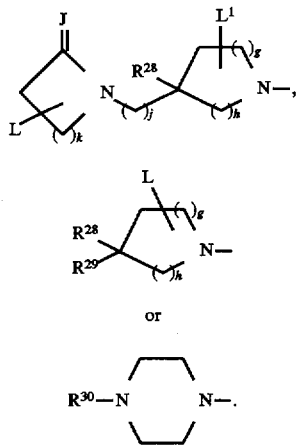

8. A compound of claim 1 wherein A is =N—$OR^1$.

9. A compound of claim 1 wherein A is =N—N($R^2$)($R^3$).

10. A compound of claim 1 wherein A is =C($R^{11}$)($R^{12}$).

11. A compound of claim 1 wherein A is =$NR^{25}$.

12. A compound of claim 7 wherein A is =N—$OR^1$.

13. A compound of claim 12 wherein X is —O—, —$NR^6$—, —N($R^6$)C(O)— or —C(O)$NR^6$—.

14. A compound of claim 12 wherein T is $R^4$-aryl.

15. A compound of claim 12 wherein Q is benzothienyl.

16. A compound of claim 12 wherein $R^{6a}$, $R^{7a}$, $R^{8a}$ and $R^{9a}$ are each H.

17. A compound of claim 12 wherein Z is

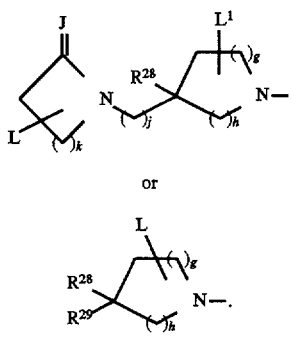

or

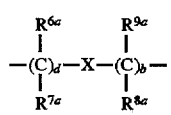

18. A compound of claim 1 wherein Q is benzothienyl, T is $R^4$-aryl, R is H, a is 1, A is =$NOR^1$, $$-(C)_d-X-(C)_b-$$
with $R^{6a}, R^{7a}$ on first C and $R^{9a}, R^{8a}$ on second C is —$CH_2$—O—$CH_2$, —$CH_2$—N($R^6$)C(O)—, —$CH_2NR^6CH_2$— or $CH_2C(O)NR^6$—, and Z is

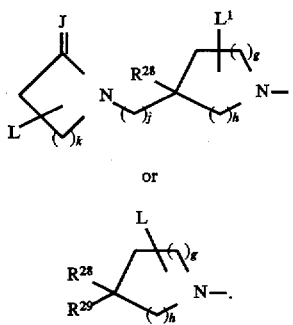

or

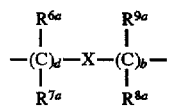

19. A compound of claim 18 wherein T is $R^4$-phenyl and $$-(C)_d-X-(C)_b-$$

is —$CH_2$—O—$CH_2$ or —$CH_2$—N($R^6$)C(O)—.

20. A compound of claim 18 wherein $R^1$ is H, alkyl, —$(CH_2)_n$—G, —$(CH_2)_p$—M—$(CH_2)_n$—G or —C(O)N($R^6$)($R^7$), wherein M is —O— or —C(O)N($R^9$)— and G is —$CO_2R^6$, —$OR^6$, —C(O)N($R^6$)($R^9$), —C(=$NOR^8$)N($R^6$)($R^7$), —C(O)N($R^9$)($R^4$-heteroaryl) or $R^4$-heteroaryl.

21. A compound of claim 1 selected from:

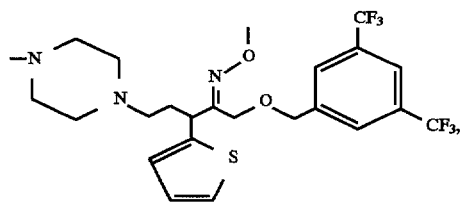

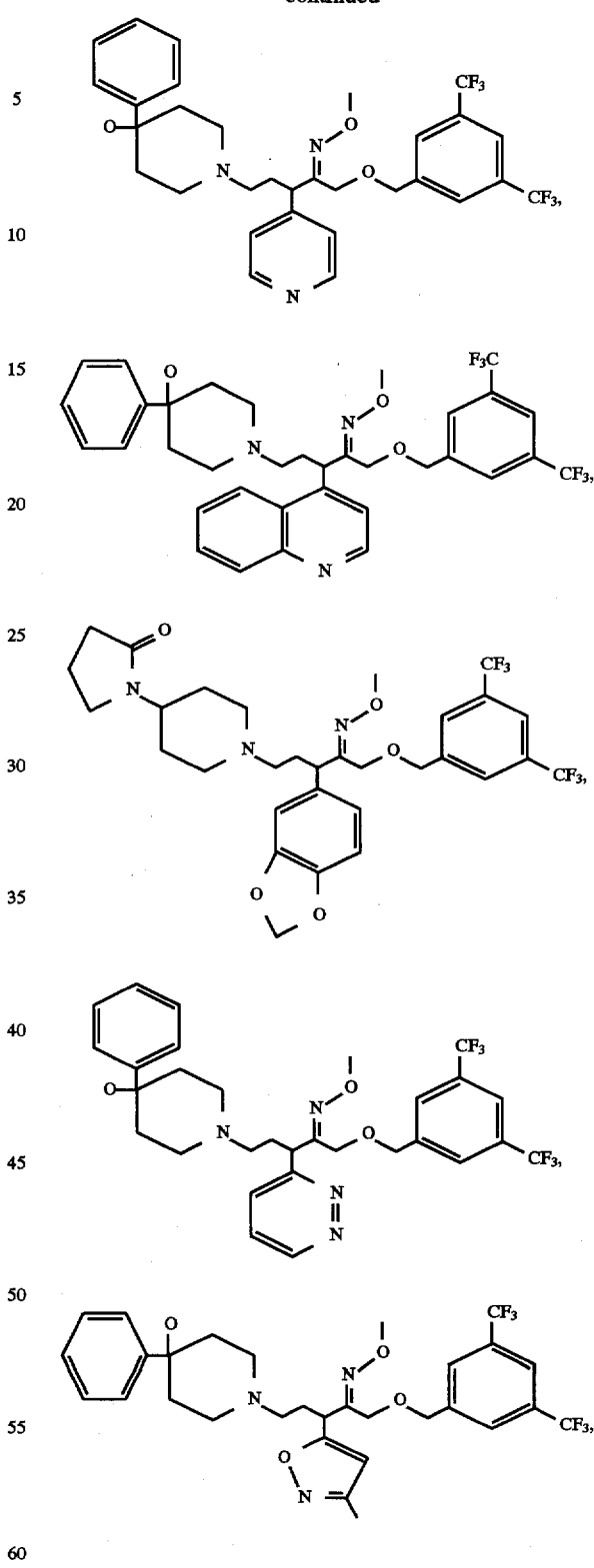

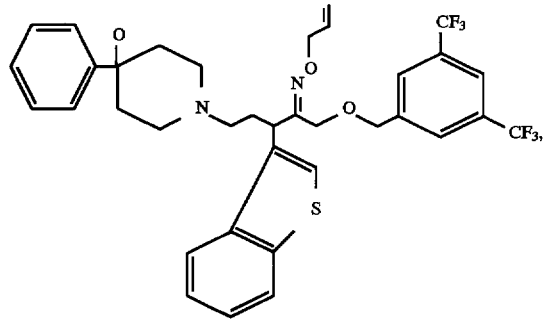
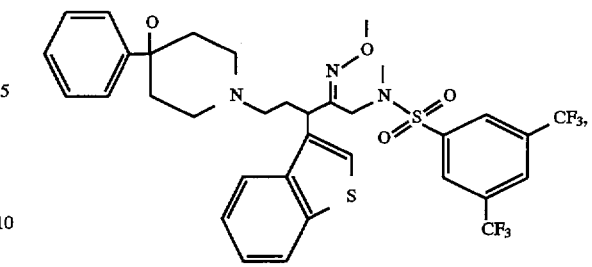
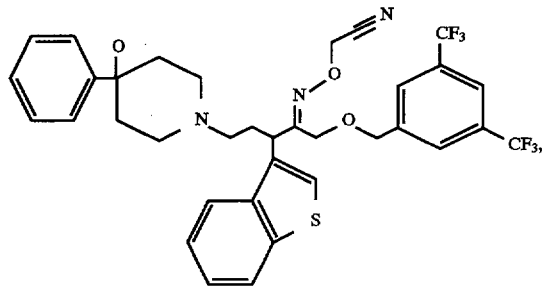
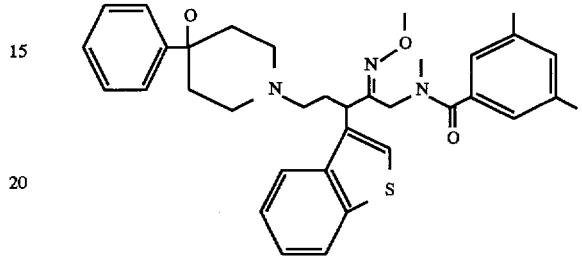
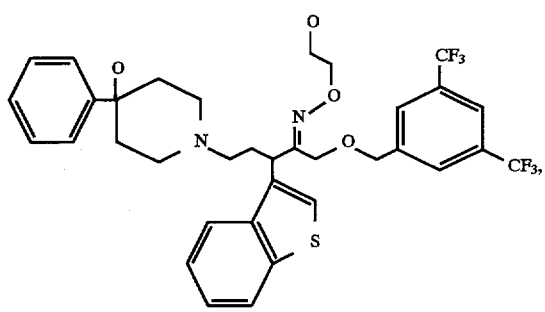
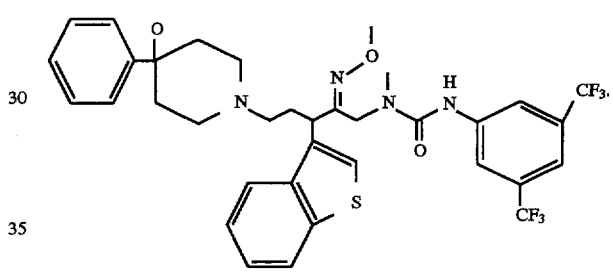
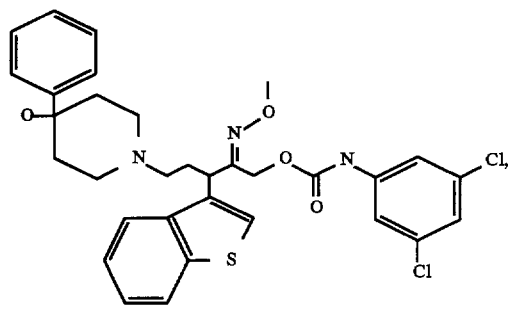

22. A pharmaceutical composition comprising an effective amount of a compound of claim 1 and a pharmaceutically acceptable carrier.

23. A method of treating asthma, cough, bronchospasm, central nervous system diseases, inflammatory diseases and gastrointestinal disorders comprising administering an effective amount of a compound of claim 1 to a mammal in need of such treatment.

* * * * *

UNITED STATES PATENT AND TRADEMARK OFFICE
CERTIFICATE OF CORRECTION

PATENT NO. : 5,688,960

DATED : NOVEMBER 18, 1997

INVENTOR(S) : BANDARPALLE B. SHANKAR

It is certified that error appears in the above-identified patent and that said Letters Patent is hereby corrected as shown below:

In column 39, lines 20 to 21, delete

"  or morpholinyl "

In column 40, lines 20-25, delete

" 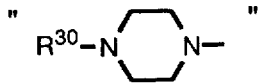 "

In column 40, line 50, delete

" 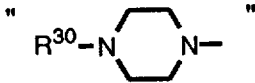 "

UNITED STATES PATENT AND TRADEMARK OFFICE
CERTIFICATE OF CORRECTION

PATENT NO. : 5,688,960

DATED : NOVEMBER 18, 1997

INVENTOR(S) : BANDARPALLE B. SHANKAR

Page 2 of 2

It is certified that error appears in the above-identified patent and that said Letters Patent is hereby corrected as shown below:

In column 41, line 60, delete "

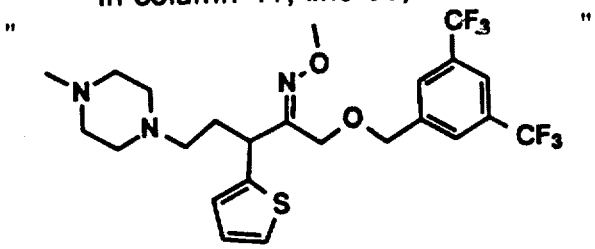

"

Signed and Sealed this

Seventh Day of April, 1998

Attest:

BRUCE LEHMAN

*Attesting Officer*  *Commissioner of Patents and Trademarks*